(12) United States Patent
Tokhtuev et al.

(10) Patent No.: US 7,491,366 B2
(45) Date of Patent: Feb. 17, 2009

(54) PORTABLE MULTI-CHANNEL DEVICE FOR OPTICALLY TESTING A LIQUID SAMPLE

(75) Inventors: Eugene Tokhtuev, Duluth, MN (US); Viktor Slobodyan, Duluth, MN (US); Christopher J. Owen, Duluth, MN (US); Christopher A. Buck, Minneapolis, MN (US); Anatoly Skirda, Duluth, MN (US); William M. Christensen, Hibbing, MN (US)

(73) Assignee: Ecolab Inc., St. Paul, MN (US)

( * ) Notice: Subject to any disclaimer, the term of this patent is extended or adjusted under 35 U.S.C. 154(b) by 656 days.

(21) Appl. No.: 11/070,647

(22) Filed: Mar. 3, 2005

(65) Prior Publication Data

US 2006/0198761 A1    Sep. 7, 2006

(51) Int. Cl.
    *G01N 21/00* (2006.01)
(52) U.S. Cl. .................................... 422/82.05
(58) Field of Classification Search ............ 422/82.05
    See application file for complete search history.

(56) References Cited

U.S. PATENT DOCUMENTS

| | | | |
|---|---|---|---|
| 3,994,590 A | 11/1976 | Di Martini et al. | |
| 4,312,593 A | 1/1982 | Baker et al. | |
| 4,797,900 A | 1/1989 | Anderson | |
| 5,083,868 A | 1/1992 | Anderson | |
| 5,604,590 A * | 2/1997 | Cooper et al. | 356/338 |
| 5,847,887 A * | 12/1998 | Ogura et al. | 359/822 |
| 5,872,361 A | 2/1999 | Paoli et al. | |
| 6,404,500 B1 | 6/2002 | Schneider et al. | |
| 6,487,349 B2 * | 11/2002 | Wach et al. | 385/115 |
| 6,836,332 B2 | 12/2004 | Mosley et al. | |
| 6,844,934 B2 | 1/2005 | Retzaff et al. | |
| 2003/0058450 A1 * | 3/2003 | Mosley et al. | 356/436 |
| 2003/0067612 A1 * | 4/2003 | Ivarsson | 356/600 |

FOREIGN PATENT DOCUMENTS

| | | | |
|---|---|---|---|
| JP | 10325800 A | * | 12/1998 |
| WO | WO 85/01579 A1 | * | 4/1985 |
| WO | WO 02/095454 A2 | * | 11/2002 |

OTHER PUBLICATIONS

Machine Translation of JP 10325800 A.*
Instruction Manual, "C 114 Multiparameter Turbidity & Free and Total Chlorine," Hanna Instruments, pp. 1-35.

* cited by examiner

*Primary Examiner*—Walter D Griffin
*Assistant Examiner*—Natasha Young
(74) *Attorney, Agent, or Firm*—Shumaker & Sieffert, P.A.

(57) ABSTRACT

A portable multi-channel device for optically testing of a liquid sample includes a controller; and a sample holder with a cylindrical sample compartment and at least two optical channels respectively for measuring turbidity of the sample liquid and for measuring one other optical property of the sample liquid. Each of the optical channels including: a light source placed at one end of the channel, a main detector placed across the sample compartment from the light source, a reference detector for measuring an intensity of light emitted by the light source, and an excitation focusing optic for directing a light emitted by the light source through the sample compartment towards the main detector. Signals from the reference detector of the channel, the main detector of the channel, and another main detector of another channel perpendicular to the channel are processed by the controller to evaluate the turbidity of the liquid sample.

32 Claims, 16 Drawing Sheets

PORTABLE MULTI-CHANNEL DEVICE FOR OPTICALLY TESTING A LIQUID SAMPLE

BACKGROUND OF THE INVENTION

1. Field of the Invention

The invention generally relates to a portable device for testing a liquid sample, and more particularly to a multi-channel device for optically testing at least the turbidity, free chlorine, total chlorine and color of surface water, drinking water, processed water or the like.

2. Description of Related Arts

Water, intended for human use and consumption, should be free of harmful chemicals and disease-causing bacteria or other microorganisms. A chlorine gas or a chlorine solution is added to water for disinfection and control of microorganisms. Testing a residual chlorine concentration after water treatment is a very important step because chlorine is known to react with organic matter in the water to form trihalomethanes (THMs), a suspected carcinogen. Free chlorine is defined as the concentration of residual chlorine in water present as dissolved gas (Cl2), hypochlorous acid (HOCl), and/or hypochlorite ion (OCl—) Combined chlorine is defined as the residual chlorine existing in water in chemical combination with ammonia or organic amines which can be found in natural or polluted waters. Total chlorine is the sum of free and combined chlorine. Two other important parameters usually tested for drinking water are turbidity and color. Turbidity itself has no health effects, however, it can interfere with disinfection and provide a medium for microbial growth. Turbidity may indicate the presence of disease causing organisms. Color is most commonly caused by dissolved organic matter, but it may be produced by dissolved mineral matter. All those parameters: free chlorine, total chlorine, turbidity and color are the most required for routine water evaluation.

Turbidity and color can be measured using optical methods. Chlorine (free and total) can be measured using calorimetric methods when specific chemicals changing their color in chlorine presence are added to water sample and chlorine concentration can be evaluated by intensity of color produced in those chemicals. Another method also can be used to measure chlorine in water (electrochemical, ion chromatography and others).

For other applications it might be needed to measure higher levels of color, turbidity and chlorine than limits specified for drinking water. On the current market there is no such portable meter, which has a high sensitivity to measure low levels and a large range to measure high levels of analytes.

There are several commercially available turbidimeters, such as Hach 2100P Portable Turbidimeter, LaMotte 2020 Portable Turbidimeter, and combinations of turbidimeter with a colorimetric chlorine meter, such as Hanna Instruments C 114 Turbidity and Chlorine Meter. They only provide several separate meters for evaluate different parameters of drinking water, rather than any color channel integrally formed and functioning with turbidity channels. They also fail to provide performance for testing water according to current regulations, such as EPA 180.1 or ISO 7027 standard.

There are two standard specifications for turbidity measurement that are generally in use worldwide. These are the International Standard ISO 7027 (Water quality—Determination of Turbidity, International Standard, Third Edition, 1999-12-15) and the USEPA 180.1 (Nephelometric Method 2130 B, Standard Methods for the Examination of Water and Wastewater, 1989). Both methods measure the intensity of light scattered at 90 degrees to the path of incident light. The specification of the ISO standard is more stringent and requires the use of a monochromatic light source.

Hach 2100P Portable Turbidimeter requires a big sample volume (15 ml), but supports only a small turbidity range (1000 NTU maximum). In addition, it is inconvenient to use since it needs a special oil to prepare sample vials for testing of low turbidity water. LaMotte 2020 Portable Turbidimeter also supports a small turbidity range (1100 NTU maximum) with a low accuracy for a low turbidity level. Hanna Instruments C 114 Turbidity and Chlorine Meter supports an ever smaller turbidity range (only 50 NTU maximum) with a low accuracy for a low turbidity level, as well as a small chlorine range.

There are many patents, such as U.S. Pat. Nos. 3,994,590, 4,312,593, 4,797,900, 5,083,868, 5,872,361, which describe methods and devices for measuring turbidity, color, or chlorine. Each of them has only one channel for measuring one parameter, rather than multiple channels for measuring multiple parameters.

U.S. Pat. No. 6,404,500 describes a multi-channel colorimetric device. This device has multiple light emission diodes (LEDs) and a radiation absorption cell. It provides a dual-purpose detector 29, i.e., a color detector+turbidity scatter channel in FIG. 5. However, most commercially available LEDs have manufacturing variations such that their various emitting intensities result in direct deviation in output absorption signals. The multi-channel colorimetric device thus has a low stability. In addition, its mathematics used for output signal evaluation was developed for out-dated, low memory, and low computational power microcontrollers. Moreover, the process involves complicated normalized absorption equations, which are not so convenient, strait forwarded and fast as look-up tables with polynomial interpolation or direct polynomial interpolations from multiple calibration points. One of its embodiments, which converts radiation absorption data into a digital wave form, has a very low sensitivity and bad time response for low intensity optical signals when frequencies of output signals are as low as 1-5 Hz. It also fails to answer how to measure an optical signal, which produce output less than 1 Hz, for a time period as short as 100 milliseconds. This is a typical problem in measuring low turbidity or high absorption in real time conditions.

U.S. Pat. No. 6,836,332 describes an instrument for testing fluid characteristics. It has multiple channels with LEDs and photovoltaic detectors for measuring multiple parameters, such as spectral transmittance, turbidity and fluorescence. However, its design has low sensitivity and stability. As mentioned, LEDs have unstable emitting intensity, spectral distribution, and spatial distribution of emitted radiation. It fails to employ reference detectors or focusing members to compensate such instability.

U.S. Pat. No. 6,844,934 describes an optical design of turbidity which includes two emitters, two detectors, a transparent cylindrical tube with liquid and lenses between emitters and the transparent cylindrical tube. The turbidity sensor in FIG. 6 has one light source channel, one scatter-signal detector, and one reference/direct signal detector placed 90 degrees from each other. However, it only applies focusing properties in a horizontal plane. In the tube section which is perpendicular to the tube section as shown on the FIG. 4, there is no focusing means and focusing properties evaluation is not valid. In addition, the optical turbidimeter does not comply with EPA 180.1 as it does not use any tungsten lamp as a light source. It also does not comply with ISO 7027 because there was no focusing member on the detector side to form an aperture angle between 10° degree. and 20° degree. in the water sample. Moreover, its big size is not convenient or portable.

Currently, there is no portable sensor for measuring color, turbidity and chlorine in water against standards specified for drinking water with high sensitivity to measure low levels and a wide range of analyses.

SUMMARY OF THE INVENTION

It is an object of the present invention to produce a portable multi-channel device for optically testing of liquid samples, especially for drinking water testing for chlorine, turbidity and color.

It is another object of the present invention to improve sensitivity and accuracy of a portable optical device by using micro focusing optics with light sources and detectors.

It is another object of the present invention to produce a portable multi-channel device with optical parameters which are compatible EPA 180.1 or ISO 7027 standard using spherical and cylindrical lenses to compensate an astigmatism of cylindrical sample vial.

It is further object of the present invention to produce a portable multi-channel device with an improved stability using reference detectors to monitor variations in emitter output.

It is also an object of the present invention to improve stability of a portable optical device by using an orientation ring to eliminate variation in optical properties due to different position of sample vial.

Other objects and advantages of the present invention may be seen from the following detailed description.

BRIEF DESCRIPTION OF THE DRAWINGS

The foregoing and additional features and characteristics of the present invention will become more apparent from the following detailed description considered with reference to the accompanying drawings in which like reference numerals designate like elements and wherein.

DETAILED DESCRIPTION OF THE INVENTION

Figure 1:
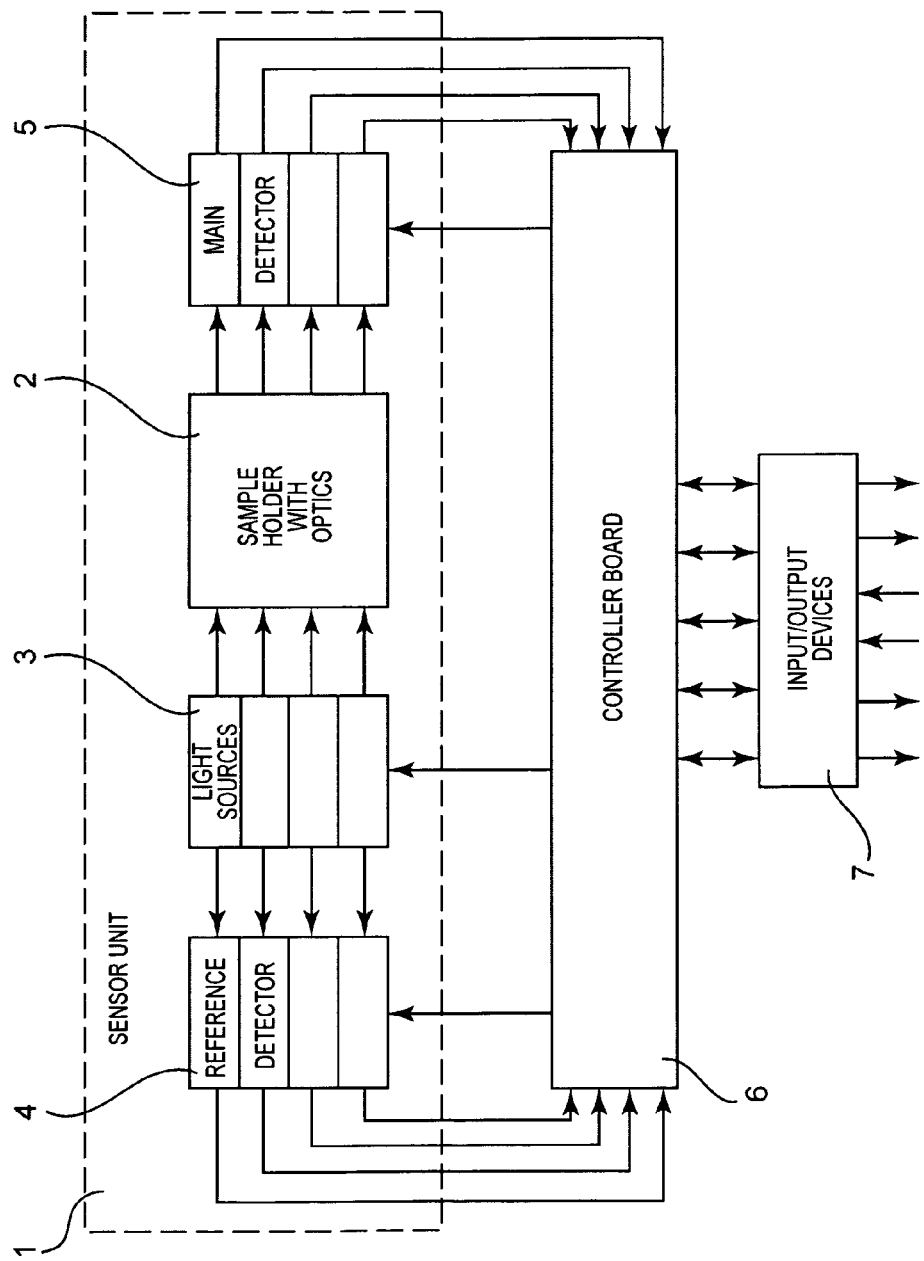
FIG. 1 shows a block diagram of a portable multi-channel device according to the invention.

FIG. 1 shows the block diagram of a portable multi-channel device 1000 of the invention. The portable multi-channel device 1000 includes a sensor unit 1, a sample holder 2 with optics, light sources 3, reference detectors 4, main detectors 5, and a controller board 6 therein. The portable multi-channel device 1000 monitors optical properties of a liquid sample placed in the sample holder 2 and evaluates chlorine, color or turbidity of the liquid sample. The controller board 6 is connected to input/output devices 7, such as a keypad, a display, or analog and digital output connectors.

Figure 2A:
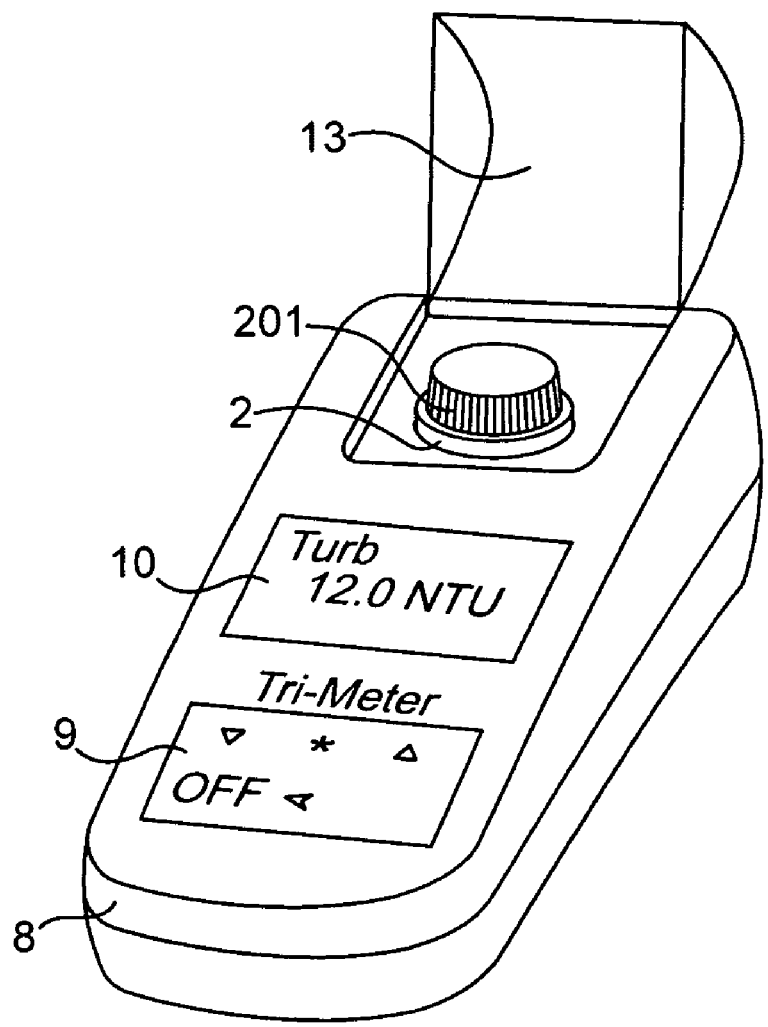
FIG. 2A shows a prospective view of the portable multi-channel device in FIG. 1.
Figure 2D:
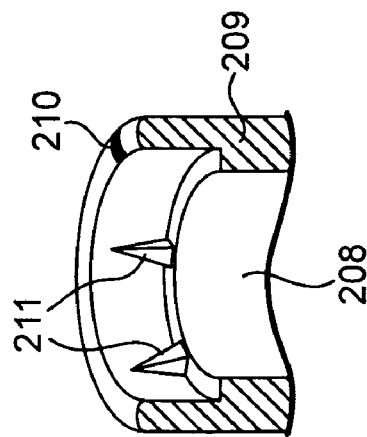
FIG. 2B shows an explored view of the sample vial, an orientation ring and a vial cap according to the invention.
FIG. 2C shows the vial with the cap and the orientation ring on, and FIG. 2D shows the inside of a sample holder of the portable multi-channel device in FIG. 1.
Figure 4:
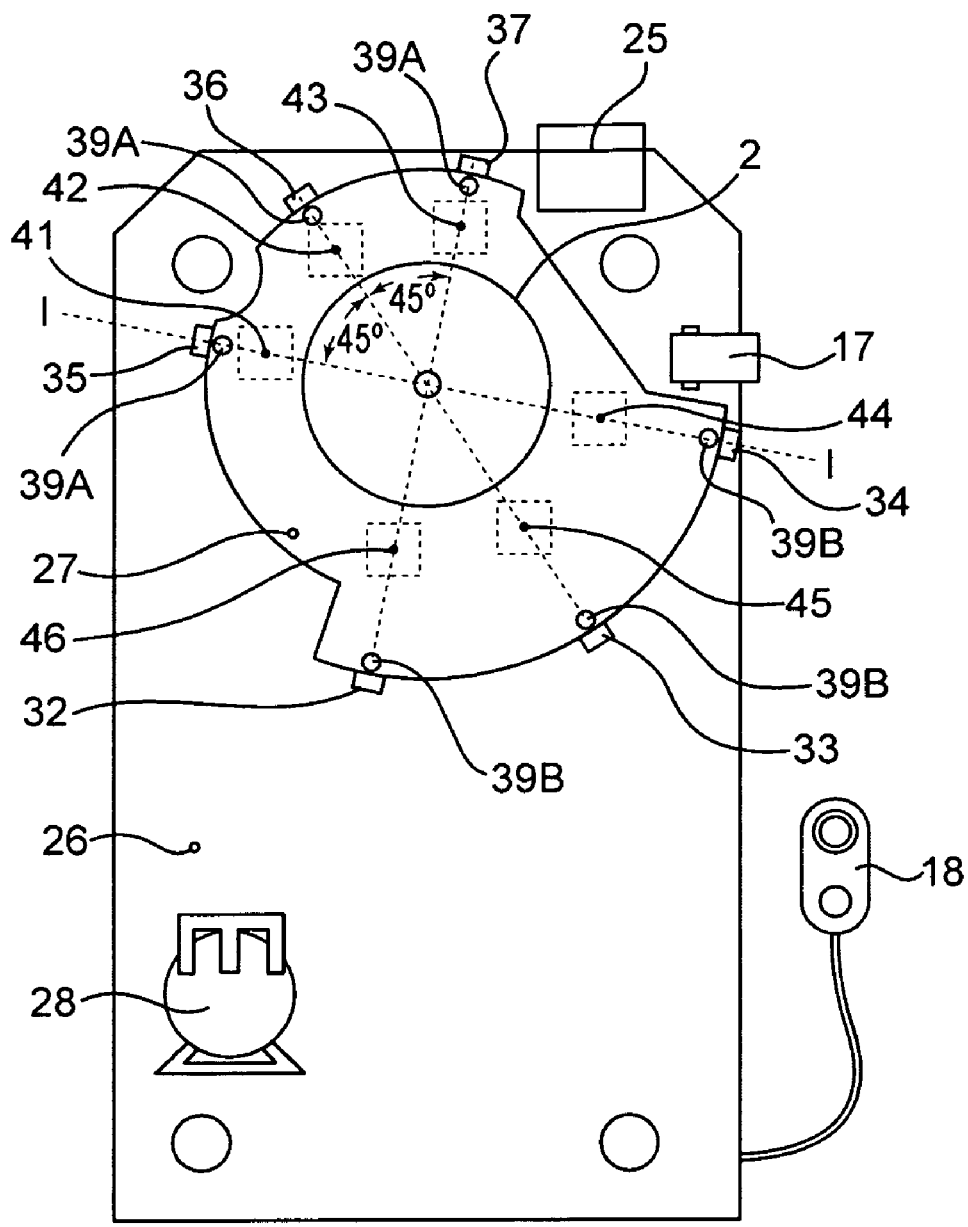
FIG. 4 shows a bottom view of the controller board with installed sample holder in FIG. 3.

The portable multi-channel device 1000 shown at the FIG. 2A has three channels to measure turbidity, color and chlorine (Tri-Meter). The portable multi-channel device 1000 has a first optical channel for measuring the turbidity using optical scattering in a visible or infrared range of spectra, a second optical channel for measuring the color using light transmittance in a visible or ultraviolet range of spectra, and a third optical channel for measuring the chlorine concentration using light transmittance in a visible range of spectra after applying a chemical compound changing color in presence of chlorine. As shown in FIG. 4, two of the optical channels being arranged symmetrically to the remaining optical channel and passing the axis of a cylindrical sample compartment to be explained later.

The channels may be located on different planes inside of the sample holder 2 as shown in U.S. Pat. No. 6,836,332 which is hereby incorporated by reference.

Figure 2C:
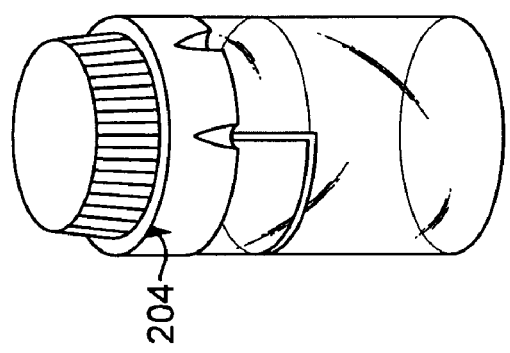
Figure 2B:
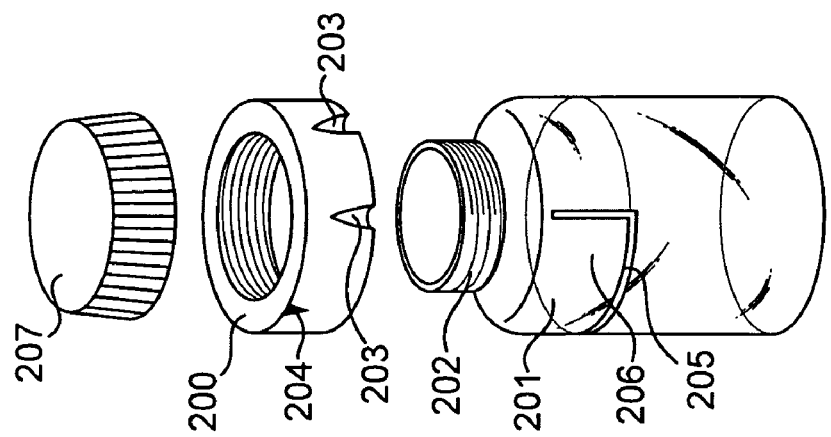

The portable multi-channel device 1000 (FIG. 2A) further includes a housing 8, a key-pad 9, a matrix liquid crystal display (LCD) 10, a transparent sample vial 201 with a cap and centering ring, and an opaque cover 13. The opaque cover 13 protects the sample vial 201 against ambient light during measurement. The housing 8 has dimensions of 90 mm×70 mm×175 mm. The sample vial 201 is a standard 10 ml glass vial. The standard 10 ml glass vials are economic and convenient; however, they are not specified for optical measurements due to their uneven optical quality. Optical properties of the vials are different form one vial to another, and even for the same vial in from one spot to another. To overcome the problem of their unevenness so as to achieve high accuracy, the invention provides an orientation ring 200 set on the sample vial 201 as shown in FIG. 2B. The orientation ring 200 is provided over the neck 202 of the vial 201 by being slid thereon. The orientation ring 200 has an inner diameter 0.1-0.3 mm smaller than the neck diameter of the vial 201 to provide a press fit therebetween. The opening at the top of the orientation ring 200 has an inner diameter 1-3 mm smaller than the neck diameter of the vial 201 to prevent the orientation ring 200 from being over-slid down the vial neck 202. A dark marker 204 is made onto the upper cylindrical outer edge of the orientation ring 200. At the lower cylindrical outer edge of the orientation ring 200, there are several orientation members, e.g., vertical tilted grooves 203.

There is a level mark 205 at the vial 201 to show the recommended level for a liquid sample 206. A cap 207 seals the vial 201 to ensure a proper positioning of the orientation ring 200. A cylindrical sample compartment 208 is accommodated by a wall 209 of the sample holder 2. The sample holder 2 is made from an opaque material and has an opaque cover and an opaque insert to fill all the space therein except the sample compartment 208 (accommodating the vial 201) and 3 cylindrical channels (accommodating the color, turbidity, and chlorine light sources and optics) with their axes perpendicular to the axis of the sample compartment 208, and 6 cylindrical vertical grooves (for accommodating 6 detectors and optics). Three light sources and three main detectors are positioned near the ends of the three cylindrical channels opposite to the ends with positive lenses. The three cylindrical channels may be located at one identical plane or in different planes inside of the sample holder. Three reference detectors are placed on near the three main detectors respectively and optically communicating with the three light sources through the vertical grooves. Details will be described in conjunction with FIG. 6A later.

The wall 209 has two inner diameters: one lower and narrower diameter for accommodating the vial body, and one upper and wider diameter for accommodating the orientation ring 200 set on the vial neck 202. The wall 209 of the sample holder 2 further has a positioning marker 210 made on its top cylindrical rim surface, and several tilted ribs 211 protruding from the wall 209 towards the sample compartment 208.

To correctly position the sample vial 201 (FIG. 2C) into the sample compartment 208 of the sample holder 2, the marker 204 should be placed against the positioning marker 210 on the wall 209 of the sample holder 2. With such an orientation mechanism, the tilted grooves 203 of the orientation ring 200 are pressed against the tilted ribs 211 on the wall 209 of the sample holder 2. Each time, the sample vial 201 gets on the same position during zero measurement, calibration and actual measurements. The orientation mechanism improves reading stability 20-50 times better than the prior art since the orientation ring 200 always brings the sample vial 201 to the same position.

Figure 3:
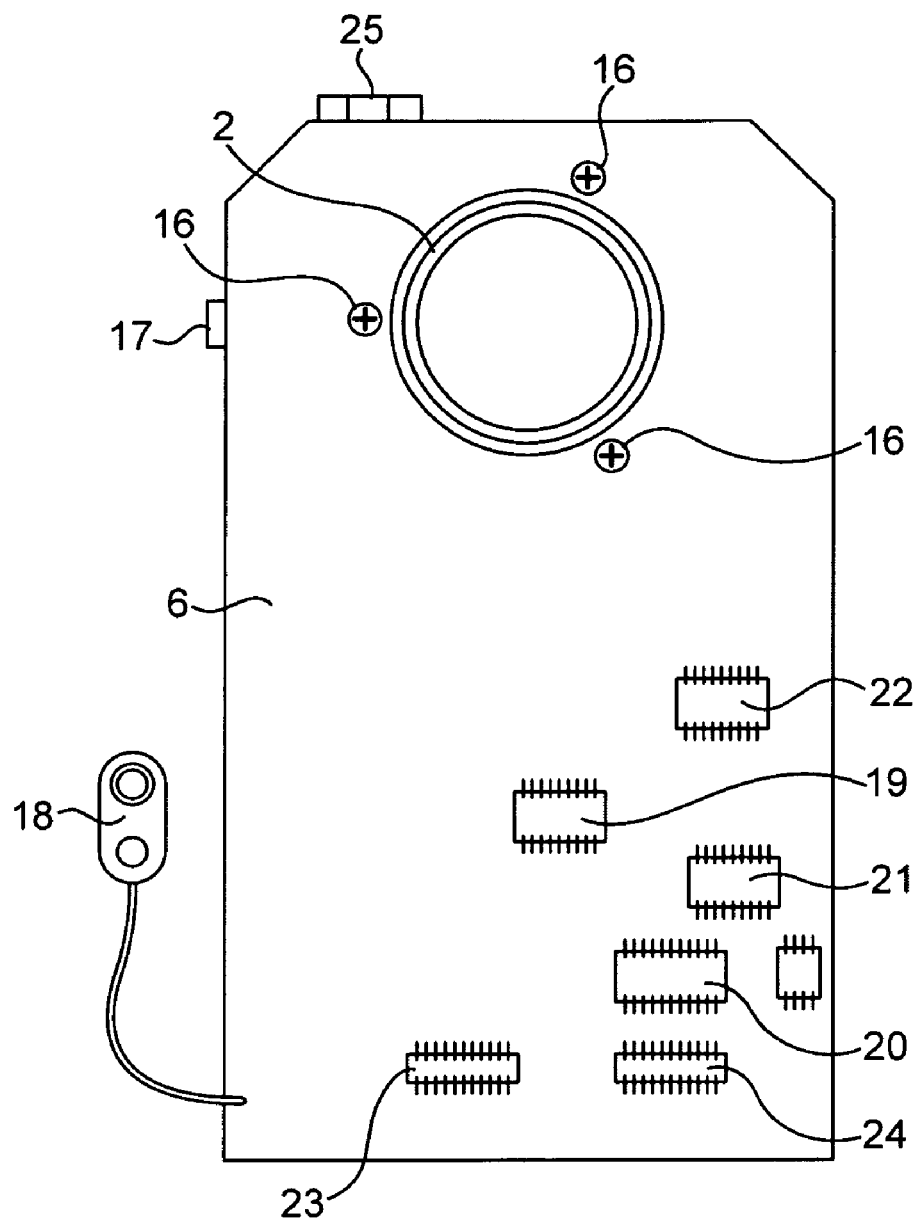
FIG. 3 shows a top view of the controller board with installed sample holder according to a first embodiment of the portable multi-channel device of the invention.

Inside the housing 8 of the portable multi-channel device 1000 (FIG. 3), there is the controller board 6 where the sample holder 2 is attached with screws 16. A processor 19, a memory 20, a calendar chip 21, and a RS-232 converter 22 are also attached to the front side of the controller board 6. The controller board 6 receives external power through a 9V power connector 17 or power from a 9V battery through a battery connector 18. The processor 19 uses calibration data stored in the memory 20, and time and date data stored in the calendar chip 21. The RS-232 converter 22 converts data from the processor 19 to provide a standard RS-232 protocol. The keypad 9 and the LCD display 10 are connected to the controller board 6 through respective connectors 23, 24. A standard RS-232 cable is connected to a RS-232 connector 25.

FIG. 4 shows the back side of the controller board 6 attached with the sample holder 2 and a Li-battery 28. The Li-battery 28 provides power to the calendar chip 21 for storing calendar over three years. The sample holder 7 has cavities at approximately 4, 5 and 6 o'clock positions for accommodating three light sources: an IR LED or EPA tungsten lamp with an output peak at 860 nm (turbidity channel) 32, a green LED with an output peak at 525 nm (chlorine channel) 33, and a UV LED with an output peak at 375 nm (color channel) 34. FIG. 4 also shows a first adjustable flat mirror (for the color channel and the scattered turbidity channel) 35, a second adjustable flat mirror (for the chlorine channel) 36, a third adjustable flat mirror (for the direct turbidity channel) 37, three main detectors 41, 42, 43 and three reference detectors 44, 45, 46 are under the sample holder (shown in dash lines), three plastic screws 39A for securing the flat mirrors 35, 36, 37, and three plastic screws 39B for securing light sources. Alternatively, the adjustable flat mirrors are shaped like a column with a flat end facing outside, and a 45-degree end facing toward the sample compartment 208. The structures and functions of these components will be explained in details later.

Figure 5:
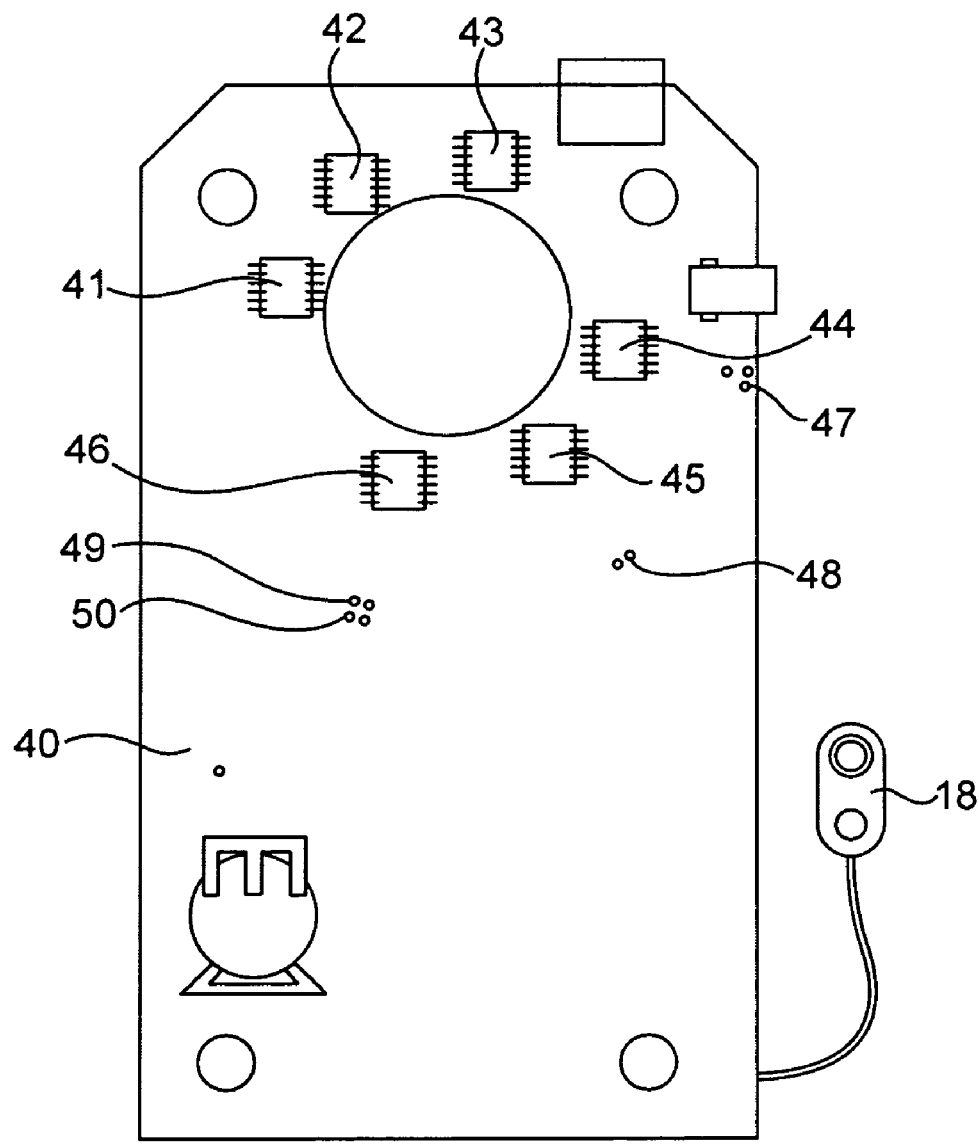
FIG. 5 shows a bottom view of the controller board outside of the sample holder in FIG. 3.

The portable multi-channel device 1000 has six detectors attached to the back side of the controller board 6 (FIG. 5). The six detectors are photodiodes with current or voltage outputs. Alternatively, the six detectors are photodiodes with frequency outputs. For example, TSL230RD by Texas Advanced Optoelectronic Solutions Inc. (Plano, Tex.) is adopted as the detectors to narrow the testing distance, to make the device small, and with a higher range (10-100 times higher than the traditional photodiode).

The six detectors include three main detectors 41, 42, 43 placed in each of the three channels across the sample holder 2 opposite to the three light sources 32, 33, 34 to measure direct signals from the three light sources 32, 33, 34, and three reference detectors 44, 45, 46 respectively next with the three light sources 32, 33, 34 (closer toward the main detectors but not on the excitation channel between one corresponding main detector and one corresponding light source) to provide a constant reference signal during measurements so as to monitor variations in the respective light source. FIG. 5 also shows the contact holes 47, 48, 49 for the UV LED (color channel) 34, the green LED (chlorine channel) 33, and the IR LED or EPA tungsten lamp (turbidity channel) 32 to be soldered therein.

The first main detector 41 measures a direct color signal form the UV LED 34 and a scattered signal at the 90° to the light source 32 (an IR LED or EPA tungsten lamp) for turbidity measurements. The second main detector 42 measures a direct chlorine signal form the green LED 33. The third main detector 43 measures a direct turbidity signal form the light source 32. A computational program is stored in the memory 20 to be executed by the processor 19 to evaluate turbidity, color and chlorine using the following equations involving the following fourteen parameters. The first seven parameters are output signals of the six detectors 41-46 measured during factory calibration and the other seven parameters are output signals of the six detectors 41-46 measured during routine measurements. Since the first main detector 41 works in two modes (the color channel and the scattered turbidity channel), only seven parameters from six detectors are used.

$U1cc$, $U1ct$—output signals from the first main detector 41 (color channel and scattered turbidity channel) during calibration and saved in the memory 20

$U2c$—an output signal from the second main detector 42 (chlorine channel) during calibration and saved in the memory 20

$U3c$—an output signal from the third main detector 43 (direct turbidity channel) during calibration and saved in the memory 20

U4c—an output signal from the first reference detector 44 (color channel) during calibration and saved in the memory 20

U5c—an output signal from the second reference detector 45 (chlorine channel) during calibration and saved in the memory 20

U6c—an output signal from the third reference detector 46 (direct turbidity channel) during calibration and saved in the memory 20

U1mc, U1mt—output signals from the first main detector 41 (color channel and scattered turbidity channel) during measurement U2m—an output signal from the second main detector 42 (chlorine channel) during measurement U3m—an output signal from the third main detector 43 (direct turbidity channel) during measurement U4m—an output signal from the first reference detector 44 (color channel) during measurement U5m—an output signal from the second reference detector 45 (chlorine channel) during measurement U6m—an output signal from the third reference detector 46 (direct turbidity channel) during measurement Each of the following four operational modes uses four or six of the above-mentioned parameters for evaluating raw signals for appropriate channels. Two or three of the used parameters of each mode are taken from the memory 20 as results of last calibration, and two or three of the remaining used parameters are measured during current measurement. Raw signals are used in respective linearization equations to obtain linearized results. Subsequently, the linearized results are applied to temperature correction equations to obtain final corrected measurement results. Each mode uses a set of calibration coefficients which are set individually for each portable multi-channel device 1000 during factory calibration. Blank parameters are set during factory calibration. However, it is recommended for better accuracy to recalibrate blank values with each new vial or even at the beginning of each test.

Turbidity Scattering Mode

The turbidity scattering mode includes measuring the light transmitted via the vial 201 (direct channel), the light scattered at 90 degrees (scattered channel) and the reference light from the light source (reference channel). First of all, the operational mode is set as "Turbidity Scattering" Secondly, the relevant calibration coefficients Xt, At, Bt, Ct, Dt, Et, Ft, Gt, and blank parameters U1ct, U6c, U3c are retrieved from the memory 20. Thirdly, a sample holder 12 containing a liquid sample is positioned in place for testing. Fourthly, press "Scan Sample" such that the controller turns on the light source, measures detector signals, calculates a corrected turbidity signal according to the equations below and shows the result on display. The calibration of the turbidity modes depends on the type of light source 32 used, e.g. a tungsten lamp or an IR LED.

$$\text{Raw Signal } Tr = (U1mt/U6m - U1ct/U6c)/[(U3m/U6m)/(U3c/U6c)] \quad (1)$$

$$\text{Linearized Turbidity Signal } Ts = Xt^*At^*[Tr^*(1+Bt^*Tr+Ct^*Tr^2+Dt^*Tr^3)+Et] \quad (2)$$

$$\text{Corrected Turbidity Signal } Tc = Ts^*[1+Ft^*(tm-tc)+Gt^*(tm-tc)^2] \quad (3)$$

Where Xt—a turbidity scaling coefficient for a customer use

At, Bt, Ct, Dt, Et—linearization coefficients for the turbidity mode

Ft, Gt—temperature correction coefficients for the turbidity mode tm—temperature during measurements tc—temperature during calibration Turbidity Attenuation Mode The turbidity attenuation mode includes measuring the light transmitted via the vial 201 (direct channel) and the reference light from the light source (reference channel). First of all, the operational mode is set as "Turbidity Attenuation." Secondly, the relevant coefficients Xd, Ad, Bd, Cd, Dd, Ed, Fd, Gd and blank parameters U6c, U3c are retrieved from the memory 20. Thirdly, a sample holder 12 containing a liquid sample is positioned in place for testing. Fourthly, press "Scan Sample" such that the controller turns on the light source, measures detector signals, calculates a corrected turbidity signal according to the equations below and shows the result on display. The calibration of the turbidity modes depends on the type of light source 32 used, e.g. a tungsten lamp or an IR LED.

$$\text{Raw Signal } Dr = \log[(U3c/U6c)/(U3m/U6m)] \quad (4)$$

$$\text{Linearized Attenuation Signal } Ds = Xd^*Ad^*[Dr^*(1+Bd^*Dr+Cd^*Dr^2+Dd^*Dr^3)+Ed] \quad (5)$$

$$\text{Corrected Attenuation Signal } Dc = Ds^*[1+Fd^*(tm-tc)+Gd^*(tm-tc)^2] \quad (6)$$

Where Xd—an attenuation scaling coefficient for a customer use

Ad, Bd, Cd, Dd, Ed—linearization coefficients for the attenuation mode

Fd, Gd—temperature correction coefficients for the attenuation mode tm—temperature during measurements tc—temperature during calibration Color Mode The color mode starts with setting the operational mode as "Color." Secondly, the relevant coefficients Xc, Ac, Bc, Cc, Dc, Ec, Fc, Gc and parameters U1cc, U4c, are retrieved from the memory 20. Thirdly, a sample holder 12 containing a liquid sample is positioned in place for testing. Fourthly, press "Scan Sample" such that the controller turns on the light source, measures detector signals, calculates a corrected color signal according to the equations below and shows the result on display.

$$\text{Raw Signal } Cr = \log[(U1cc/U4c)/(U1mc/U4m)] \quad (7)$$

$$\text{Linearized Color Signal } Cs = Xc^*Ac^*[Cr^*(1+Bc^*Cr+Cc^*Cr^2+Dc^*Cr^3)+Ec] \quad (8)$$

$$\text{Corrected Color Signal } Cc = Cs^*[1+Fc^*(tm-tc)+Gc^*(tm-tc)^2] \quad (9)$$

Where Xc—a color scaling coefficient for a customer use

Ac, Bc, Cc, Dc, Ec—linearization coefficients for the color mode

Figure 6A:
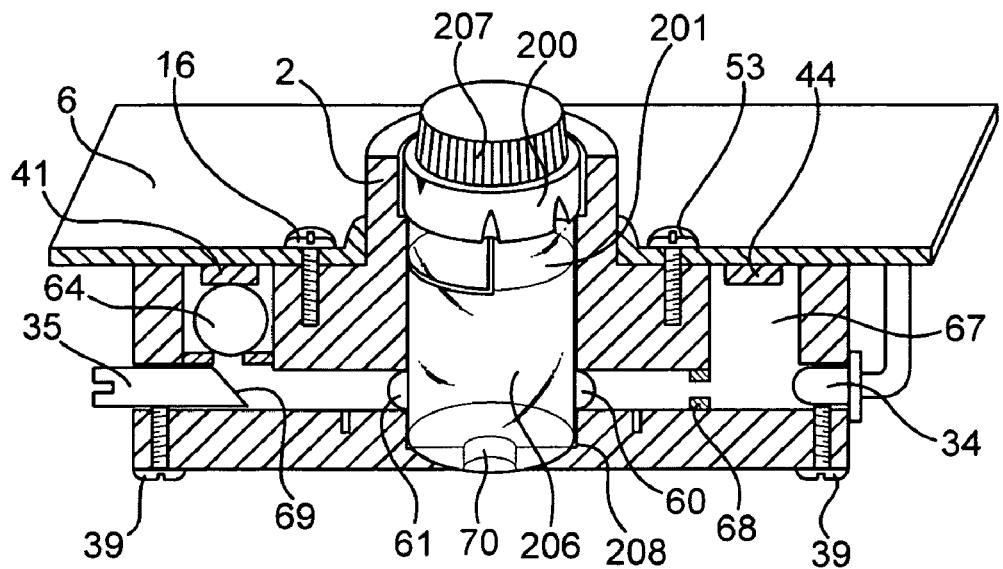
FIG. 6A shows a cross-sectional view of the controller board within sample holder taken along I-I in FIG. 4.

Fc, Gc—temperature correction coefficients for the color mode tm—temperature during measurements tc—temperature during calibration Chlorine Mode The chlorine mode starts with setting the operational mode as "Chlorine." Secondly, the relevant coefficients Xh, Ah, Bh, Ch, Dh, Eh, Fh, Gh and parameters U2c, U5c, are retrieved from the memory 20. Thirdly, a sample holder 12 containing a liquid sample is positioned in place for testing. Fourthly, press "Scan Sample" such that the controller turns on the light source, measures detector signals, calculates a corrected color signal according to the equations below and shows the results on the display. In another embodiment, the portable multi-channel device 1000 has four rather than one chlorine modes to measure a free chlorine with a liquid reagent and with a tablet reagent as well as a total chlorine with a liquid reagent and with a tablet reagent.

$$\text{Raw Signal } Hr = \log[(U2c/U5c)/(U2m/U5m)] \quad (10)$$

$$\text{Linearized Signal } Hs = Xh^*Ah^*[Hr^*(1+Bh^*Hr+Ch^*Hr2+Dh^*Hr3)+Eh] \quad (11)$$

$$\text{Corrected Signal } Hc = Hs^*[1+Fh^*(tm-tc)+Gh^*(tm-tc)2] \quad (12)$$

Where Xh—a chlorine scaling coefficient for a customer use.
Ah, Bh, Ch, Dh, Eh—linearization coefficients for the chlorine mode
Fh, Gh—temperature correction coefficients for the chlorine mode
tm—temperature during measurements
tc—temperature during calibration FIG. 6A shows a cross-sectional view of the controller board 6 within the sample holder 2 taken along I-I in FIG. 4. It shows the design and operation of the color channel. The screws 16 are provided to fix the sample holder 2 to the controller board 6. As described previously, the sample vial 201 with the sample liquid 206 is placed into the sample compartment 208 of the sample holder 2 and oriented with the orientation ring 200 underneath the vial cap 207. An opening 70 is made for purging of the liquid sample 206 if it is spilled into the sample compartment 208. The UV LED 34 is provided at the right end of the color channel to emit UV light with a wavelength peak at 375 nm. The UV light then travels via a diaphragm 68 with an opening of 2 mm wide, to pass excitation focusing optic (e.g., at least one positive lens) 60, to be directed through the sample compartment 208 in the sample holder 2. After passing through the sample solution 206, the transmitted UV light travels to a first sample focusing optic (e.g., a positive lens) 61 to be directed to a flat reflective surface 69 of the first adjustable flat mirror 35. the invention provides the pair of micro focusing optics 60, 61 on the emitter side and on the detector side respectively. On the other hand, the prior art, such as U.S. Pat. No. 6,844,934, only provides a lens 114 on the emitter side of the sensor.

The flat reflective surface 69 is titled about 45 degrees from the axis of the color channel. A pair of screws 39 are provided underneath the UV LED 34 and the first adjustable flat mirror 35 respectively for securing and adjusting the positions thereof. The positive lenses placed in cylindrical channels having their axis perpendicular to the axes of the sample compartment. The positive lenses 60, 61 are placed in the cylindrical color channel with their axis perpendicular to the axis of the sample compartment 208. The reflected UV light then travels to pass a second sample focusing optic (e.g., a ball lens) 64. The ball lens 64 is placed directly on the input window of the first main detector 41, and the first adjustable flat mirror 35 placed with its flat reflective surface 69 right on the cross of the axis of the positive lens 60, 61 and the axis of the ball lens 64. The first main detector 41 is soldered on the controller board 6 with its axis parallel to the axis of the sample compartment 208. Finally, the UV light reaches the first main detector (in both the color channel and in the scattered turbidity channel) 41. The first adjustable flat mirror 35 and the ball lens 64 eliminate wiring and make the whole device smaller.

The first reference detector (color channel) 44 is placed in an attenuation chamber 67 connected to a section of the channel between the UV LED 34 and the diaphragm 68 from above to collect UV light emitted from the UV LED 34 and scattered into the attenuation chamber 67. The prior art does not provide any such an attenuation chamber to attenuate light therein. The attenuation chamber 67 has dimensions of 3 mm×5 mm×6 mm and attenuates light to a level which does not cause the saturation and non-linearity for the reference detector.

The area of analysis of the channel is defined by the optical axis of the excitation focusing optics 60 and the sample focusing optics 61 displaced across the center of cylindrical sample compartment 208. Signals from the first reference detector (color channel) 44 and the first main detector (the color channel) 41 are processed by the controller board 6 to evaluate the color of the liquid sample 206 using the Color Mode equations (7)-(9)

Figure 6B:
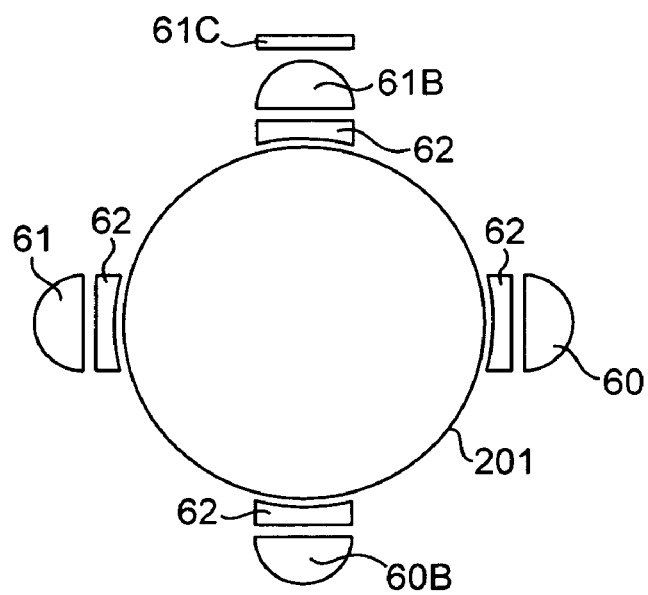
FIG. 6B shows a top view of the vial and a pair of cylindrical focusing lenses taken along II-II in FIG. 6A.

By analogy, the visible or infrared light source 32 (e.g., an IR LED or EPA tungsten lamp) is provided at the right end of the turbidity channel to emit visible or infrared light with a wavelength peak at 860 nm. The visible or infrared light then travels via a diaphragm with an opening of 2 mm wide, to pass third excitation focusing optic 60B (e.g., at least one positive lens in FIG. 6B), to be directed through the sample compartment 208 in the sample holder 2. After passing through the sample solution 206, the transmitted visible or infrared light travels to a third sample focusing optic (e.g., a positive lens) 61B to be directed by a flat reflective surface of the third adjustable flat mirror 37 to the third main detector 43. The flat reflective surface is titled about 45 degrees from the axis of the turbidity channel. A pair of plastic screws 39 are provided underneath the visible or infrared light source 32 and the third adjustable flat mirror 37 respectively for securing and adjusting the positions thereof. The scattered visible or infrared light travels to the first sample focusing optic (e.g., a positive lens) 61 of the color channel to be directed by a flat reflective surface of the first adjustable flat mirror 35 to the first main detector 41. Part of the light from the visible or infrared light source 32 scattered in attenuation cavity near the light source 32 is detected by the third reference detector 46. Signals from the third reference detector (turbidity channel) 46, the first main detector 41 (scattered turbidity channel) and the third main detector (turbidity channel) 43 are processed by the controller board 6 to evaluate the turbidity of the liquid sample 206 using the Turbidity Scattering Mode equations (1)-(3). Optionally, a pair of cylindrical negative lenses 62 (FIG. 6B) are provided between the vial 201 and the positive lenses 60, 60B, 61, 61B respectively to compensate the distortion caused by the positive cylindrical optical power, i.e., unevenness, of the cylindrical vial 201.

A fluoropolymer film 61C is placed between the third sample focusing optics 61B and the third main detector 43 to eliminate the unevenness of the vial 201. The fluoropolymer film is especially important for the attenuation turbidity channel. With the fluoropolymer film 61C, the error for low attenuation measurements such as 50NTU being decreased from +/−10 NTU to +/−1 NTU.

A fluoropolyrner film is traditionally provided with a thickness of 5, 10, 20, 30, or 50 mills and has excellent optical properties, as well as good thermal and chemical stability. The optimal thicknesses of the fluoropolymer films are 20 mills for the turbidity attenuation channel, 10 mills for the chlorine channel and 5 mills for the color and scattered turbidity channel.

The reflected visible or infrared light then travels to pass a second sample focusing optic (e.g., a ball lens) 64. The ball lens 64 is placed directly on the input window of the third main detector 43, and the third adjustable flat mirror 37 placed with its flat reflective surface right on the cross of the axis of the positive lens 60, 61 and the axis of the ball lens 64. The third main detector 43 is soldered on the controller board 6 with its axis parallel to the axis of the sample compartment 208. Finally, the visible or infrared light reaches the third main detector (in the direct turbidity channel) 43. The third adjustable flat mirror 37 and the ball lens 64 eliminate wiring and make the whole device smaller.

The third reference detector (direct turbidity channel) 46 is placed in an attenuation chamber to collect light emitted from the visible or infrared light source 32 and scattered into the attenuation chamber. Signals from the third reference detector (direct turbidity channel) 46 and the third main detector (in the direct turbidity channel) 43 are processed by the controller board 6 to evaluate the turbidity of the liquid sample 206 using the Turbidity Attenuation Mode equations (4)-(6).

In short, the mechanism for measuring turbidity includes a light source, a reference detector to measure part of the light emitted from the light source, the excitation focusing optics, the sample focusing optics, one main detector to measure the direct turbidity signal, another sample focusing optics at the 90 degrees to the first excitation focusing optics, another main detector to measure the 90 degree turbidity signal (scattered), and a fluoropolymer film placed between the sample focusing optics and the main detector for measuring the direct signal.

In a similar manner, the green LED 33 is provided at the right end of the chlorine channel to emit light with a wavelength peak at 525 nm. The green light then travels via a diaphragm with an opening of 2 mm wide, to pass a second excitation focusing optic (e.g., at least one positive lens), to be directed through the sample compartment 208 in the sample holder 2. After passing through the sample solution 206, the transmitted or scattered green light travels to a second sample focusing optic (e.g., a positive lens) to be directed to a flat reflective surface of the second adjustable flat mirror 36. The flat reflective surface is titled about 45 degrees from the axis of the chlorine channel. A pair of plastic screws 39 are provided underneath the green LED 33 and the second adjustable flat mirror 36 respectively for securing and adjusting the positions thereof. Optionally, a pair of cylindrical negative lenses 62 (FIG. 6B) are provided between the vial 201 and the positive lenses 60, 61 respectively to compensate the distortion caused by the positive optical power, i.e., unevenness, of the cylindrical vial 201.

The reflected green light then travels to pass a second sample focusing optic (e.g., a ball lens). The ball lens is placed directly on the input window of the second main detector 42, and the second adjustable flat mirror 36 placed with its flat reflective surface 69 right on the cross of the axis of the positive lens 60, 61 and the axis of the ball lens. The second main detector 42 is soldered on the controller board 6 with its axis parallel to the axis of the sample compartment 208. Finally, the light reaches the second main detector (chlorine channel) 42. The second adjustable flat mirror 36 and the ball lens 64 eliminate wiring and make the whole device smaller.

The second reference detector (chlorine channel) 45 is placed in an attenuation chamber to collect the green light emitted from the green LED 33 and scattered into the attenuation chamber. Signals from the second reference detector (chlorine channel) 45 and the second main detector (chlorine channel) 42 are processed by the controller board 6 to evaluate the chlorine of the liquid sample 206 using the Chlorine Mode equations (10)-(12), after applying a chemical compound changing color in presence of chlorine.

In other embodiments, other forms of the prismatic focusing devices described in U.S. Pat. No. 6,842,243, which is hereby incorporated by reference, are used to replace the positive lens 60, 61 or the ball lens 64. The invention applied a measuring principle (measuring the direct light and the scattered light passing through the liquid sample) different from the one described in FIG. 1 of the U.S. Pat. No. 6,842,243, i.e., measuring only the light transits through the liquid sample, reaching the analytical area 13, and then scattered therein by 90°±2.5°.

Optionally, a pair of cylindrical negative lenses 62, 62' (FIG. 6B) are provided between the vial 201 and the positive lenses 60, 61 respectively to compensate the distortion caused by the positive optical power, i.e., unevenness, of the cylindrical vial 201. The pair of cylindrical negative lenses 62, 62' may be made by (1) preparing a cubic transparent block with a center column compartment there through just sufficient for the vial 201 to pass through, i.e., approximately the diameter as the sample compartment 208, and (2) carving out two pairs of the cylindrical negative lenses 62, 62' near centers of the four side faces of the block wrapping around the column. The cylindrical negative lenses 62, 62' have a diameter of 4-6 mm to be applied to the vial 201 of 20 mm bottle.

The portable multi-channel device 1000 provides a dynamic range, ideally suitable for both low-level drinking water applications as well as monitoring high load in the field. The unique optics configuration enables the portable multi-channel device 1000 to read low levels for Turbidity (0.05 NTU), Chlorine (0.02 ppm) and Color (0.2 PCU) while also expanding to higher ranges, 0-4,000 NTUs for Turbidity, 500 PCUs for Color and 0-10 ppm for Chlorine. The portable multi-channel device 1000 is available in either EPA or ISO 7027 compliant versions and features in different languages, data logging, RS-232 interface and CE mark. The invention is commercially available as TC-3000 Tri-Meter.TM. distributed via LaMotte (Chestertown, Md.).

Figure 7:
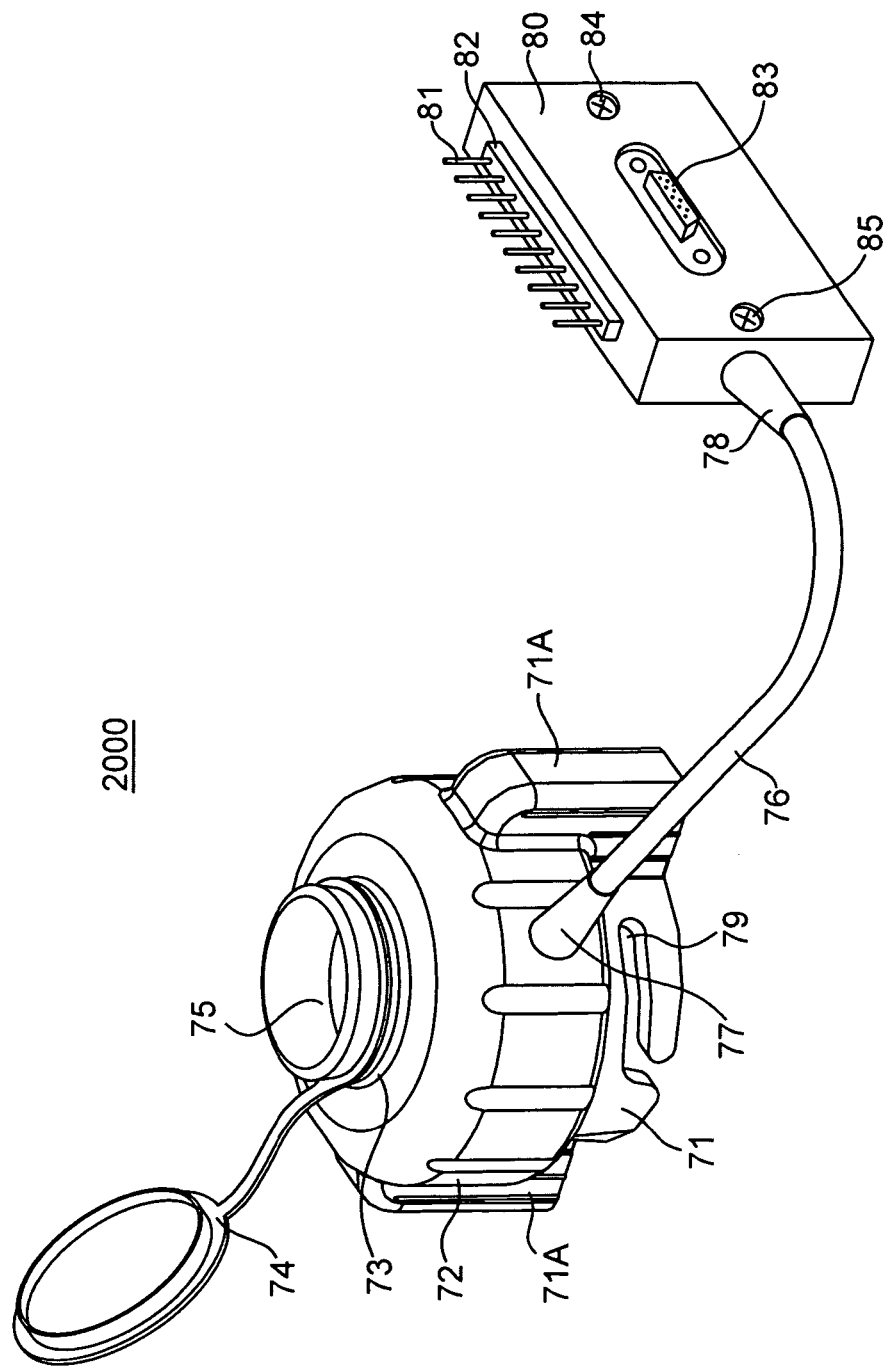
FIG. 7 shows a second embodiment of the portable multi-channel device of the invention.

FIG. 7 shows a second embodiment of a portable multi-channel device 2000 according to the invention. The portable multi-channel device 2000 includes an opaque sample holder 71 with extended wings 71A, and a controller box 80 connected to the sample holder 71 via a cable 76. The sample holder 71 has two of the optical channels for measuring turbidity using optical scattering in a visible or infrared range of spectra and for measuring color of a sample water using light transmittance in a visible or ultraviolet range of spectra similar to the channels in the portable multi-channel device 1000. However, the optical channels of the second embodiment are arranged symmetrically to an axis of the cylindrical sample compartment and passing the axis of the cylindrical sample compartment. In addition, by separating the controller from the sample holder, the second embodiment becomes smaller than the first embodiment. The sample holder has a diameter of 50 mm and a height of 45 mm, and the controller box 80 has dimensions of 60 mm.times.40 mm.times.10 mm.

Figure 9A:
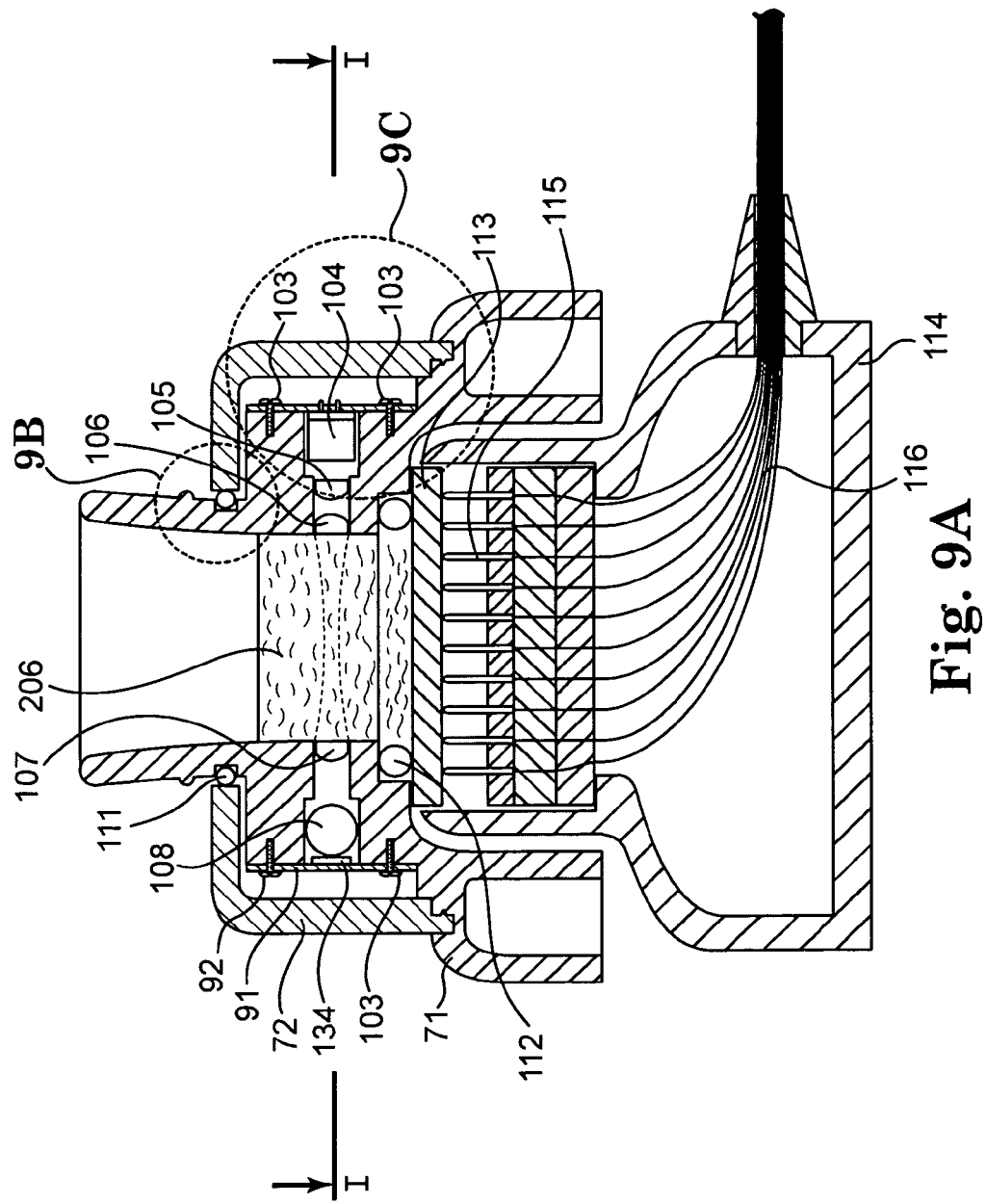
FIG. 9A shows a vertical cross-sectional view of the sample holder of the multi-channel micro sensor taken along the line I-I in FIG. 8.

Each optical channel includes a light source, a reference detector for measuring the light source intensity, an excitation focusing optics for directing a focused beam through a sample compartment in the sample holder, a main detector, a sample focusing optics for directing transmitted or scattered light to the main detector. Signals from the reference detectors and the main detectors are processed by the controller box 80 to evaluate turbidity and color of the water samples. Rather than an assemble of a controller board with sample holder in the portable multi-channel device 1000, the multi-channel device 2000 has the controller box separated from the sample holder 71 to make the housing of the sample holder even smaller. Besides the wings 71A, the sample holder 71 also has an opaque cover 72, a sealing o-ring 73, an opaque lid 74, a sample compartment 75, a strain relief 77, and a bayonet connection 79 to connect the separable bottom disk 113 (FIG. 9A). The separable disk 113 allow an easy cleaning of optical part inside the sample holder. The controller box 80 has a controller connector 81, a sealing pad 82, a RS-232 connector 83, mounting screws 84, 85, and a strain relief 78.

Figure 10A:
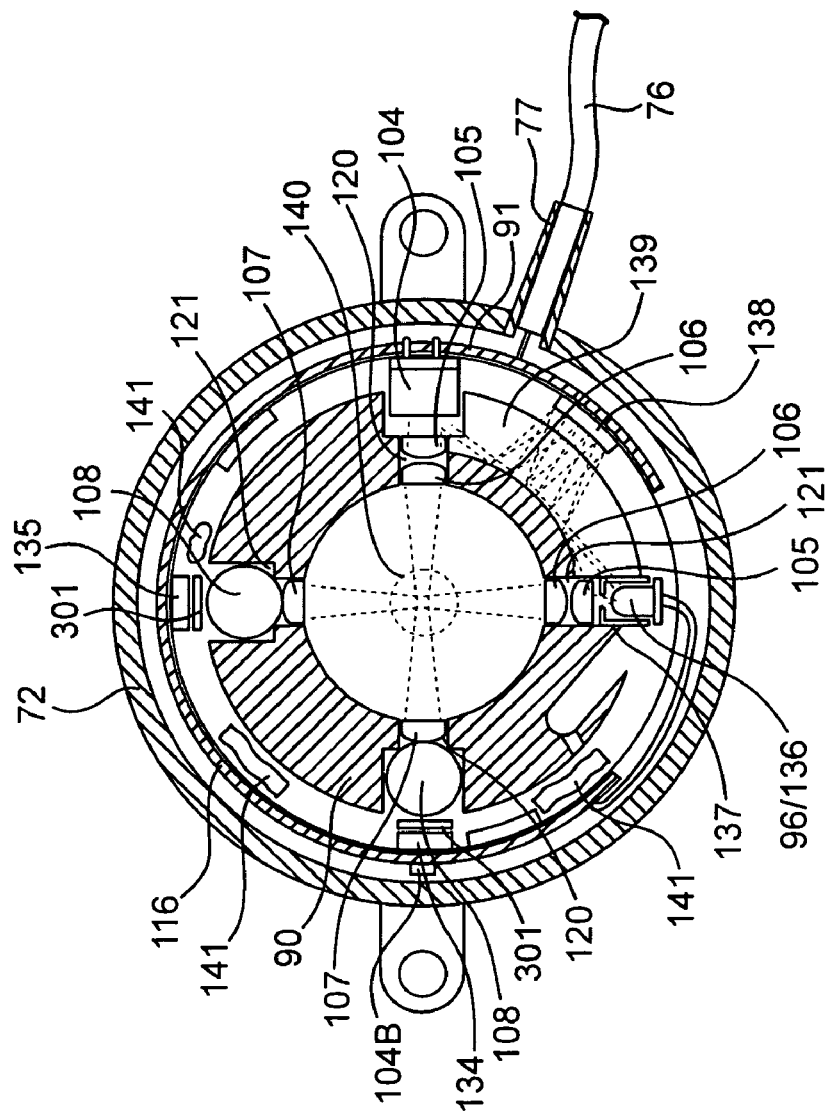
FIG. 10A shows a horizontal cross-sectional view of the sample holder of the multi-channel micro sensor with an IR LED taken along the line I-I in FIG. 9A.
Figure 10B:
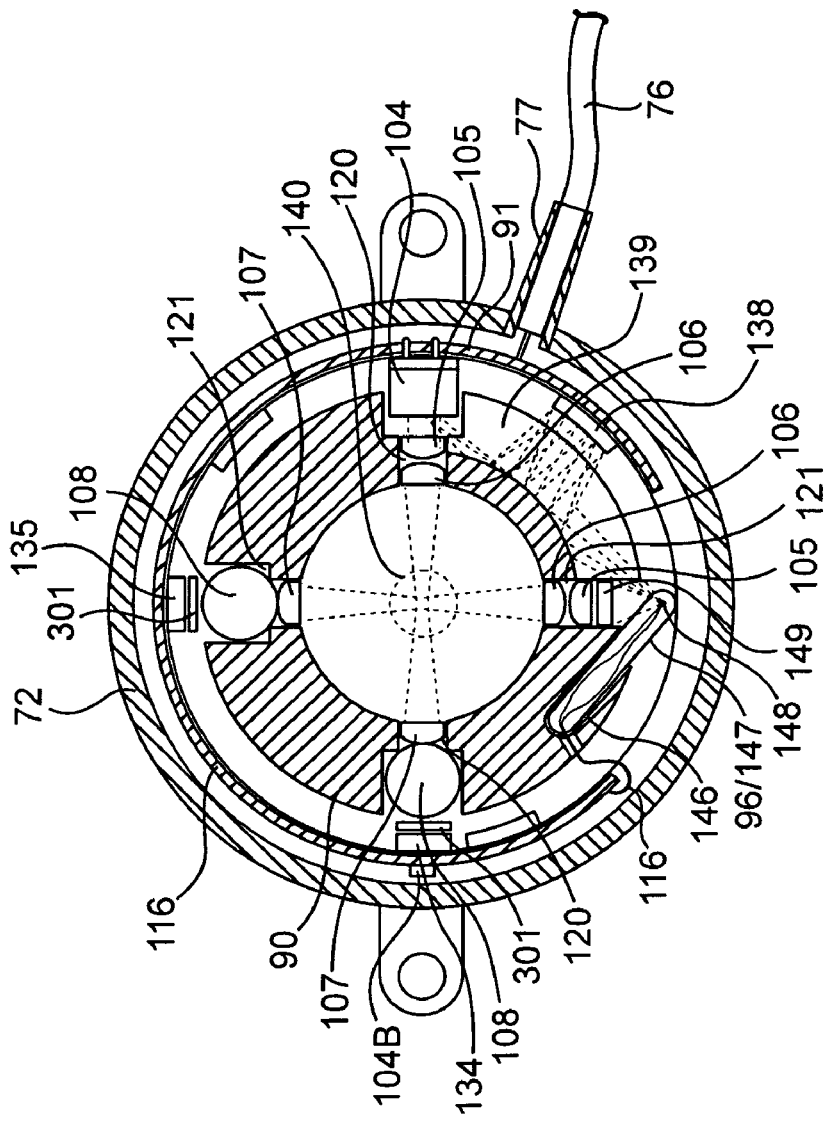
FIG. 10B shows a horizontal cross-sectional view of the sample holder of the multi-channel micro sensor with an EPA lamp taken along line I-I in FIG. 9A.

Since the embodiment does not need any sample vial 201, no cylindrical negative lenses 62, 62' to compensate the distortion caused by the positive optical power, i.e., unevenness, of the cylindrical vial 201. In addition, the lenses 106, 107 in FIGS. 9A and 10A-B are immersed in the water sample 206 such that the second embodiment provides a better sensitivity and accuracy than the first embodiment. As there is no cylindrical vial 201 with an inferior optical quality and no distortion of optical beams, the lenses 106, 107 are evaluated to work with their flat side immersed in the water sample 206.

Figure 8:
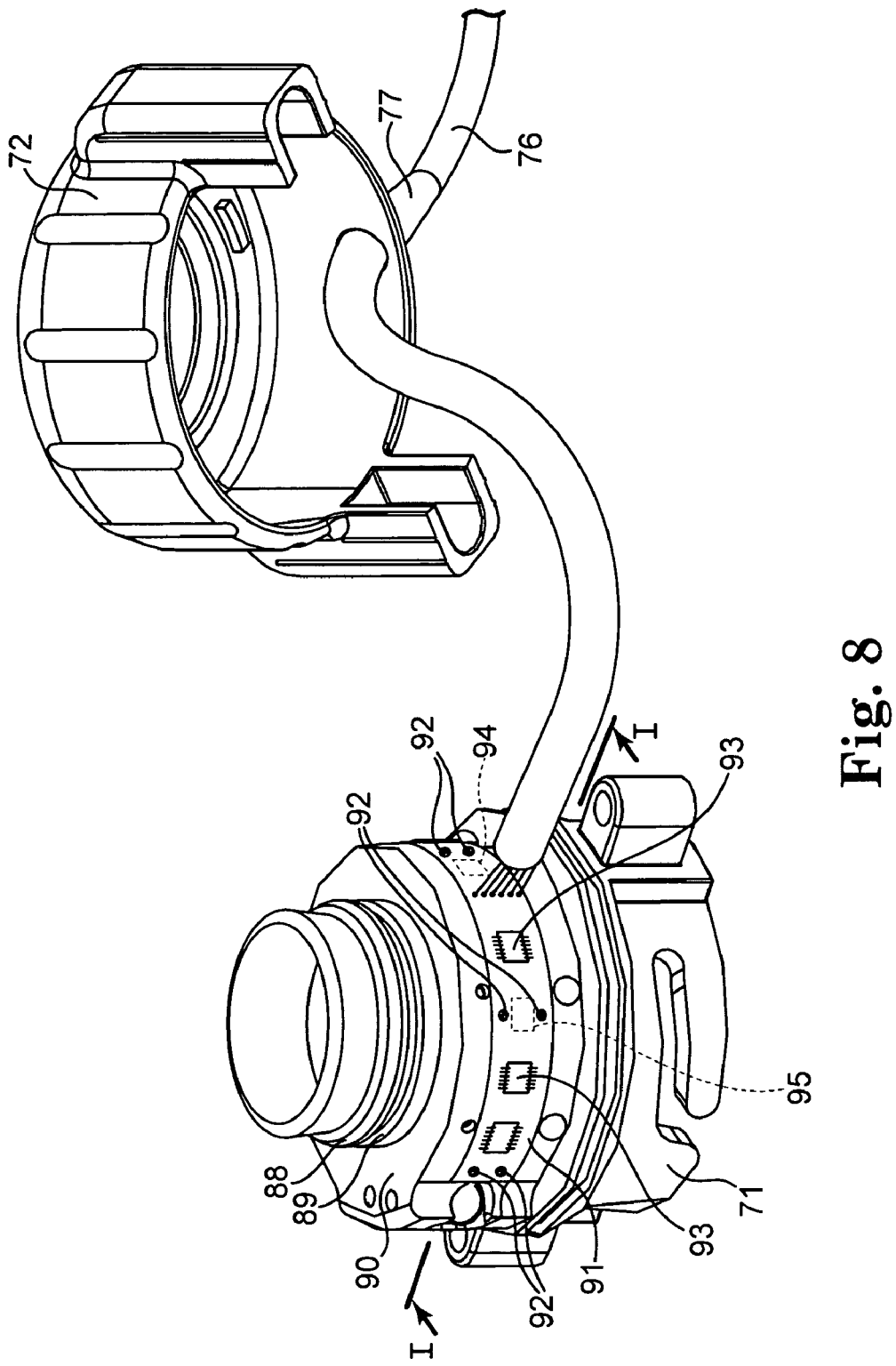
FIG. 8 shows a multi-channel micro sensor with removed cover.

FIG. 8 shows the multi-channel micro sensor 2000 with the cover 72 removed. The sample holder 71 further includes a snap rib 88 for the opaque lid 74, a groove 89 for the sealing o-ring 73, an opaque insert 90, a flexible board 91, mounting screws 92, electronic chips 93 placed on the outside surface of the flexible board 91. The screws 92 are provided to fix the sample holder 71 to the flexible board 91. FIG. 8 also shows a position 94 of first UV LED 104 (chlorine channel) placed on the internal surface of the flexible board 91, and a position 95 of a reference detector 138 placed on the internal surface of the flexible board 91.

The portable multi-channel device 2000 has only three detectors attached to the internal surface of the flexible board 91. The three detectors are photodiodes with current or voltage outputs. Alternatively, the three detectors are photodiodes with frequency outputs. FIG. 10A shows a horizontal cross-sectional view of the sample holder of the multi-channel micro sensor with an IR LED taken along the line I-I in FIG. 9A, and FIG. 10B shows a horizontal cross-sectional view of the sample holder of the multi-channel micro sensor with an EPA lamp taken along the line I-I in FIG. 9A. FIGS. 10A-B show a cylindrical color channel including a sub-channel (color channel) 120 for excitation focusing optics and a sub-channel (color channel and scattered turbidity channel) 120' for sample focusing optics. FIGS. 10A-B also show a cylindrical turbidity channel including a sub-channel (turbidity channel) 121 for excitation focusing optics and a sub-channel (turbidity channel) 121' for sample focusing optics.

The three detectors include two main detectors 134, 135 placed in each of the two channels (at 9 and 12 o'clock positions) across the sample compartment 75 opposite to two light sources 96, 104 (at 6 and 3 o'clock positions) to measure direct signals there from, and a reference detector 138 is set in-between the two light sources 96, 104, i.e., between 4-5 o'clock positions, to provide a constant reference signal during measurements so as to monitor variations in the both light sources. The main detector 134 receives an optical shift signal from a LED 104B to provide a constant shift of the frequency output for more than 10Hz. The LED 104B (FIG. 10A) is placed opposite to the main detector 134 with the flexible board 91 therebetween. The flexible board 91 is translucent and allows a small optical signal to be delivered just through the board.

The LED 104B constantly illuminates towards the main detector 134 to generate an optical shift of a "zero signal" from 0.5-1 HZ to 15-30 Hz. The "zero signal" outperforms the prior art digital wave form the detector, such as mentioned in U.S. Pat. No. 6,404,500, by 1/10 of response time. Without such an optical shift, a low turbidity signal output at 0.5-1 Hz takes at least 2 seconds (a time period) for evaluation. With the optical shift, a high turbidity signal output at 15-30 Hz can be measured in 0.1 second. The "zero signal" is a signal which corresponds to the small optical signal having low intensity due to low scattering as for analyses concentrations of 0 NTU turbidity or due to low intensity because of high absorbency as for analyses of 500 Color Units water, or 10 ppm of chlorine, or for 4000 NTU of turbidity. The prior art does not provide any such an LED for providing an optical shift.

The first main detector 134 measures a direct color signal form the UV LED 104 and a scattered signal at the 90° to the light source 96 (an IR LED or EPA tungsten lamp) for turbidity measurements. The second main detector 135 measures a direct turbidity signal form the light source 96. A computational program is stored in the memory 20 to be executed by a processor in the controller box 80 to evaluate turbidity and color using the above-mentioned equations (1)-(9).

FIG. 9A shows a cross-sectional view of the sample holder 71 of the multi-channel micro sensor 2000 taken along I-I in FIG. 8. The liquid sample 206 is poured directly into the sample compartment 75, rather than in sample vial 201 as described in the first embodiment. A replaceable non-optical sensor unit 113 is directly placed underneath the sample compartment 75, with only 0-ring 112 in-between. The replaceable non-optical sensor unit 113 is also shaped as a disk and includes at least one of a temperature sensor, a conductivity sensor, a pH sensor, an electrochemical sensor and the like. Signals generated by the non-optical sensor unit 113 are transmitted via spring contacts 115 connected with connection wires 116 which are then connected with the cable 76 to the controller box 80. The sample holder 71, the non-optical sensor unit 113, the spring contacts 115, and the connection wires 116 are supported by a base 114. The base 114 has a diameter of 50 mm.

Figure 9C:
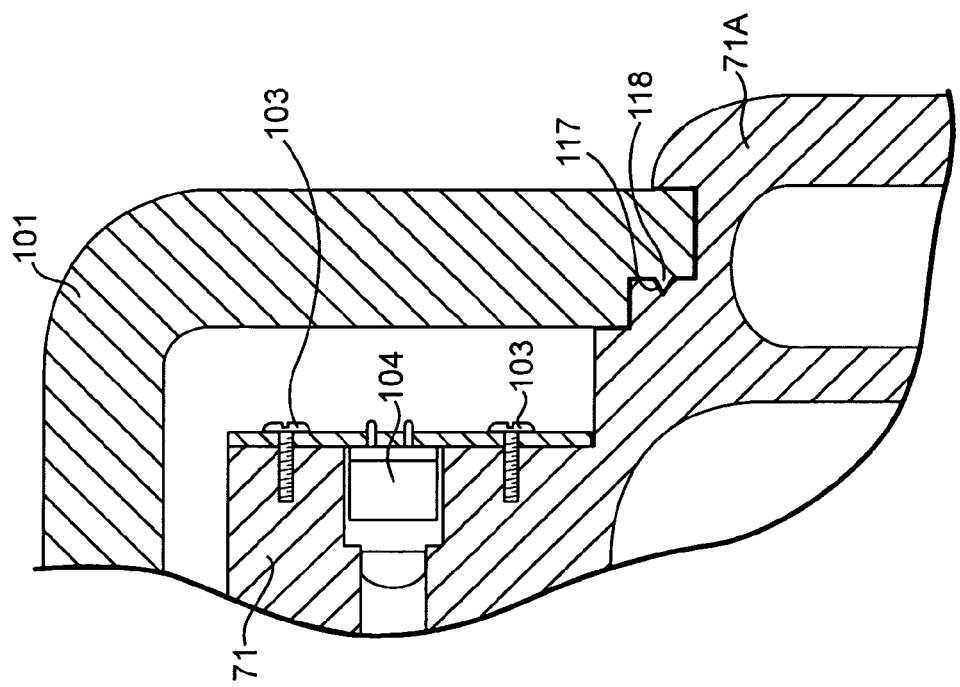
FIG. 9C shows an enlarged view of a water-tight base seal for a multi-channel micro sensor in FIG. 8.
Figure 9B:
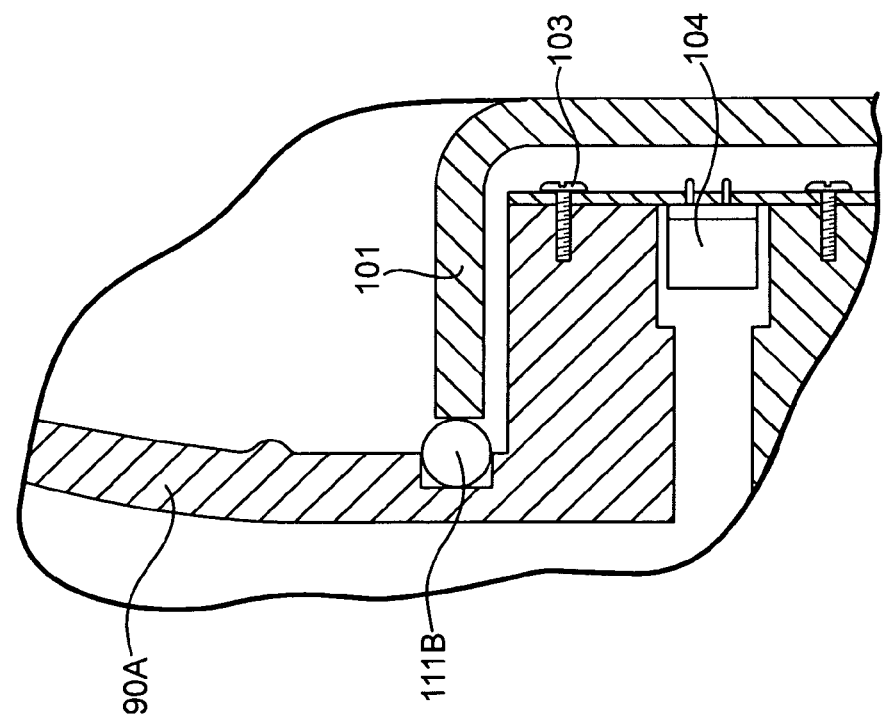
FIG. 9B shows an enlarged view of a water-tight cover seal for a multi-channel micro sensor in FIG. 8.

FIG. 9B shows an enlarged view of a water-tight cover seal for the sample compartment 75 of the multi-channel micro sensor 2000, and FIG. 9C shows an enlarged view of a water-tight base seal for the sample compartment 75 of the multi-channel micro sensor 2000. The opaque insert 90 is water-tightly placed against the cover 101 with an o-ring 111B in-between, and the opaque insert 90 is water-tightly placed against the wings 71 A of the sample holder 71 with a base snap groove 117 in the wings 71A pressed into a snap rib 118 at the rim of the cover 101.

The UV LED 104 is provided at the right end of the color channel to emit UV light with a wave length peak at 375 nm. The UV light then travels via first and second excitation focusing optics (e.g., at least one positive lens) 105, 106, to be directed through the sample compartment 75 in the sample holder 71. After passing through the sample solution 206, the transmitted or scattered UV light travels to a first sample focusing optic (e.g., a positive lens) 107 to be directed to a second sample focusing optic (e.g., a ball lens) 108. The positive lenses 105, 106, 107 are placed in the cylindrical color channel with their axis perpendicular to the axis of the sample compartment 75. The ball lens 108 is placed directly on the input window of the first main detector (in both the color channel and in the scattered turbidity channel) 134. The area of analysis 140 of the channel in the sample compartment 75 is defined by the optical axis of the excitation focusing optics 105, 106 and the sample focusing optics 107, 108 displaced across the center of cylindrical sample compartment 75. Signals from the reference detector 138 and the first main detector 134 are processed by the controller box 80 to evaluate the color of the liquid sample 206 using the Color Mode equations (7)-(9) as well as to evaluate the turbidity of the liquid sample 206 using the Turbidity Scattering Mode equations (1)-(3).

By analogy, the visible or infrared light source 96 (e.g., an IR LED or EPA tungsten lamp) is provided at the right end of the turbidity channel to emit visible or infrared light with a wave length peak at 860 nm. The visible or infrared light then travels via a diaphragm 137 with an opening of 2 mm wide, travels via first and second excitation focusing optics (e.g., at least one positive lens) 105, 106, to be directed through the sample compartment 75 in the sample holder 71. After passing through the sample solution 206, the transmitted or scattered visible or infrared light travels to a first sample focusing optic (e.g., a positive lens) 107 to be directed to a second sample focusing optic (e.g., a ball lens) 108. The positive lenses 105, 106, 107 are placed in the cylindrical turbidity channel with their axis perpendicular to the axis of the sample compartment 75. The ball lens 108 is placed directly on the input window of the second main detector (in the turbidity channel) 135. The reference detector (for a UV and IR LED, or an EPA tungsten lamp) 138 is soldered on the flexible board 91 facing toward an internal groove 139 in the opaque insert 90 to collect visible or infrared light emitted from the visible or infrared light source 96 and scattered into the internal groove 139. A light absorbing material 141 is provided to eliminate scattered light between light sources and the detectors through the scattering inside of the cover 92 between the flexible board 91 and sample holder 71. The light absorbing material 141 is also provided between the detectors to eliminate scattered light from one detector to another. FIG. 10A shows an IR LED 136 set in the diaphragm 137, while FIG. 10B shows a tungsten lamp 147 set in a lamp mounting chamber 146 with a lamp filament 148 at one end of the lamp 147 connected to the internal connection wires 116 and a blue-green glass filter 149 provided close to another end of the lamp 147. The blue-green glass filter 149 is placed on the axis of the turbidity channel between the lamp 147 and the excitation focusing optics 105 to provide spectral parameters according to the EPA 180.1 standard. The lamp mounting chamber 146 tilts away from the channel.

The area of analysis 140 of the channel is defined by the optical axis of the excitation focusing optics 105, 106 and the sample focusing optics 107, 108 displaced across the center of cylindrical sample compartment 75. Fluoropolymer films 301 are placed between the sample focusing optics 107, 108 and the main detectors 134 and 135. Signals from the reference detector 138 and the second main detector 135 are processed by the controller box 80 to evaluate the turbidity of the liquid sample 206 using the Turbidity Attenuation Mode equations (4)-(6).

Figure 11A:
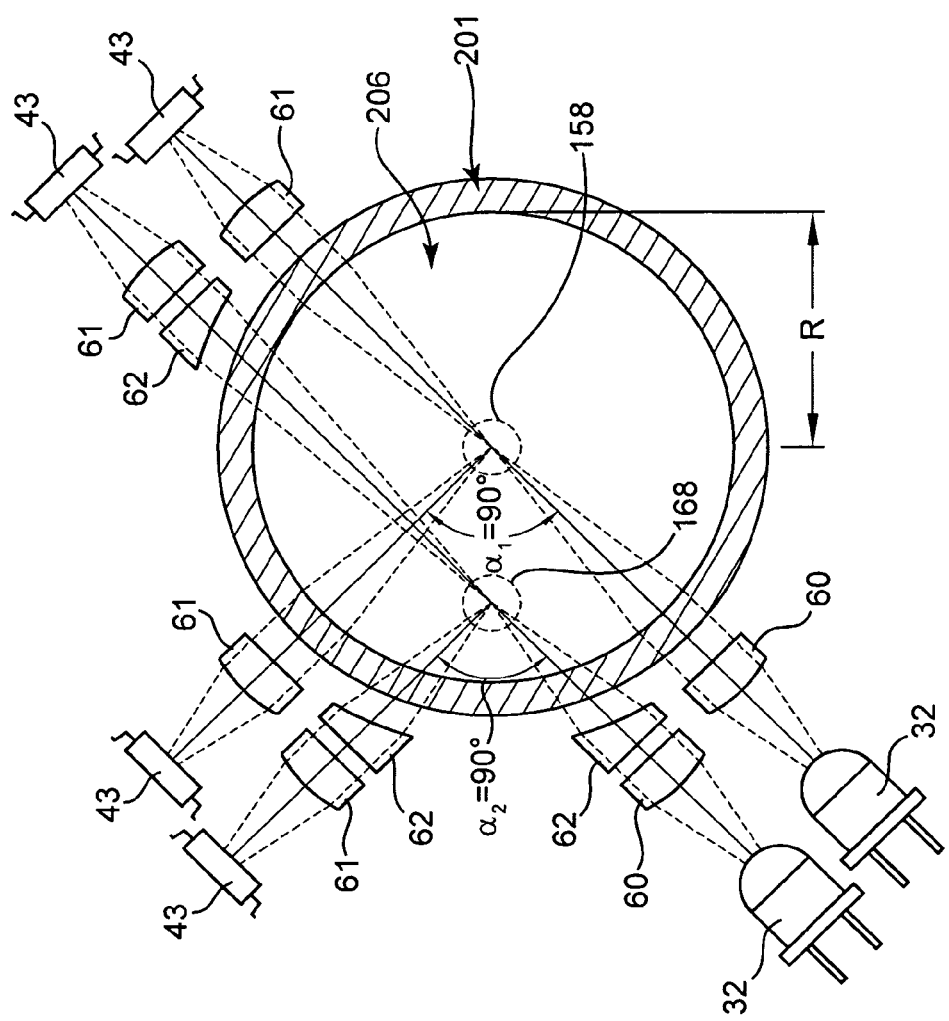
FIG. 11A shows the optical configuration of the first embodiment of the portable multi-channel device of the invention FIG. 6A and a modification thereof with a shifted area of analysis for turbidity measurements.

FIG. 11A shows the optical configuration of the first embodiment of the portable multi-channel device of the invention FIG. 6A. An area of analysis 158 of the turbidity channel of the portable multi-channel device 1000 shown in FIG. 6A is defined by the optical axis of the excitation focusing optics 60 and the sample focusing optics 61 displaced across the transparent sample vial 201. The area of analysis 158 of the turbidity channel is approximately located at the center of the transparent sample vial 201 or the cylindrical sample compartment 208. The IR LED 32 is placed at 7 o'clock position, the detector for direct signal measuring 43 is placed at 1 o'clock position, and the detector for scattered signal measuring 44 is placed at 10 o'clock position.

Figure 12:
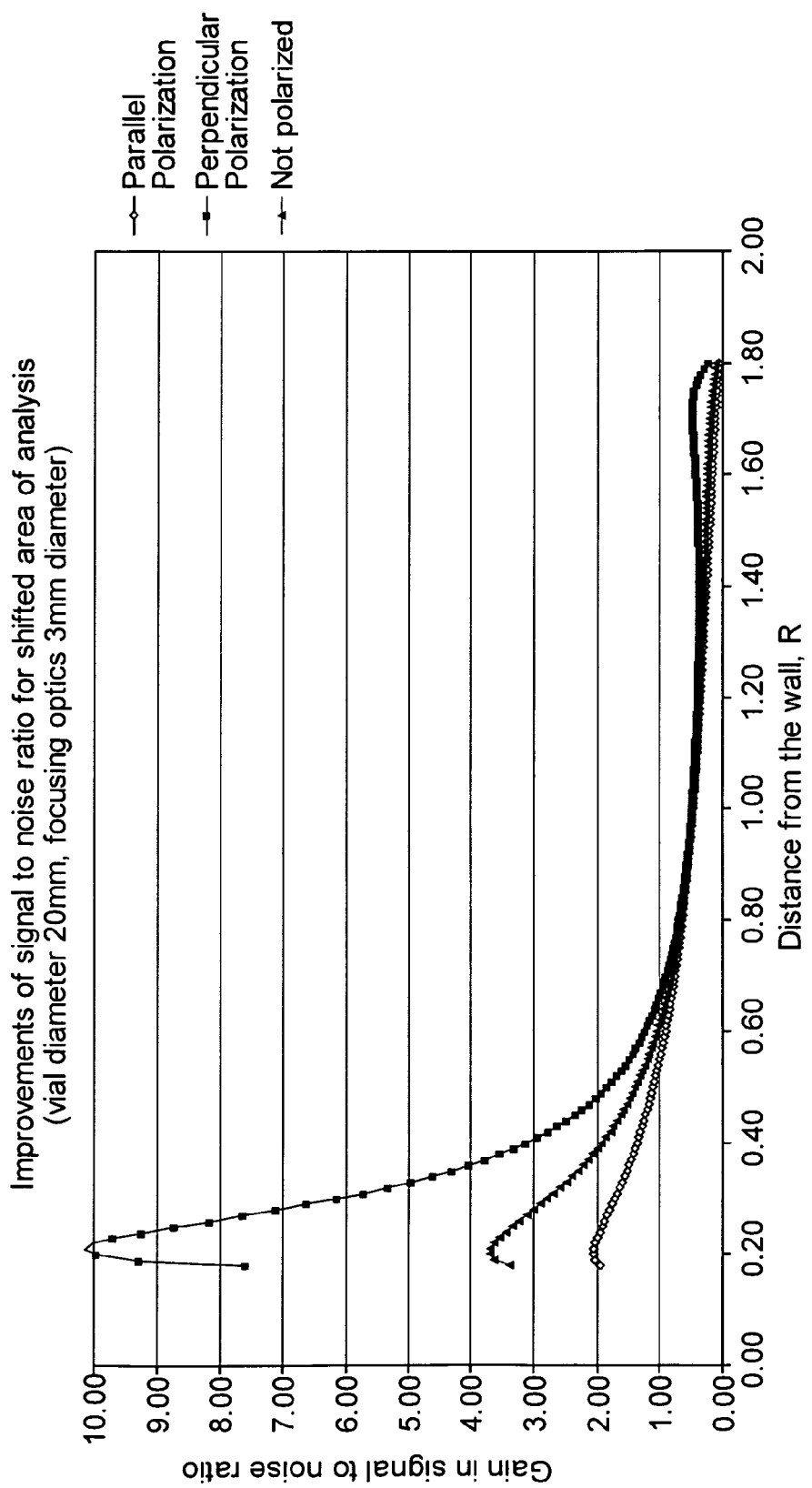
FIG. 12 shows changes in signal level for different positions of scattering points from the wall of the vial in the first embodiment of the portable multi-channel device of the invention FIG. 6A.

FIG. 11A also shows a modification of the first embodiment of the portable multi-channel device of the invention FIG. 6A with a shifted area of analysis 168 for turbidity measurements. The shifted area of analysis 168 of the turbidity channel is approximately located approximately ¼ of radius away from the center of the transparent sample vial 201 or the cylindrical sample compartment 208. As the shifted area of analysis 168 is close to the wall of the vial 201, the light in the modification does not have to travel as far as the original such that the testing range is increased to 4000-5000 NTU and the sensitivity of the modification increases about 4-5 times as shown in FIG. 12. The IR LED 32 is placed at 8 o'clock position, the detector for direct signal measuring 43 is placed at 12 o'clock position, and the detector for scattered signal measuring 44 is placed between 9 and 10 o'clock positions. The turbidity channel of the modification is in parallel with the turbidity channel of the first embodiment of the portable multi-channel device of the invention. The detector for scattered signal measuring 44 is placed $\alpha 2 = 90$ degree to the turbidity channel of the modification, as the detector for scattered signal measuring 44 is placed $\alpha 1 = 90$ degree to the turbidity channel of the first embodiment of the portable multi-channel device of the invention.

Three cylindrical negative lenses 62, 62', 62" are provided between the vial 201 and the positive lenses 60, 61, 61' respectively to compensate the distortion caused by the positive optical power, i.e., unevenness, of the cylindrical vial 201. The three cylindrical negative lenses 62, 62', 62" may be made by a similar way as the pair of cylindrical negative lenses 62, 62' in FIG. 6B. First, preparing a cubic transparent block with a center column compartment there through just sufficient for the vial 201 to pass through, i.e., approximately the diameter as the sample compartment 208. Second, carving out two pairs of the cylindrical negative lenses 62, 62' away from the centers of the four side faces of the block wrapping around the column corresponding to the positions of the turbidity channel of the modification in FIG. 11A. Third, applying only three cylindrical negative lenses 62, 62', 62' as the three cylindrical negative lenses 62, 62', 62", since the cylindrical negative lenses 62" is shaped exactly the same as the cylindrical negative lenses 62'.

Figure 11B:
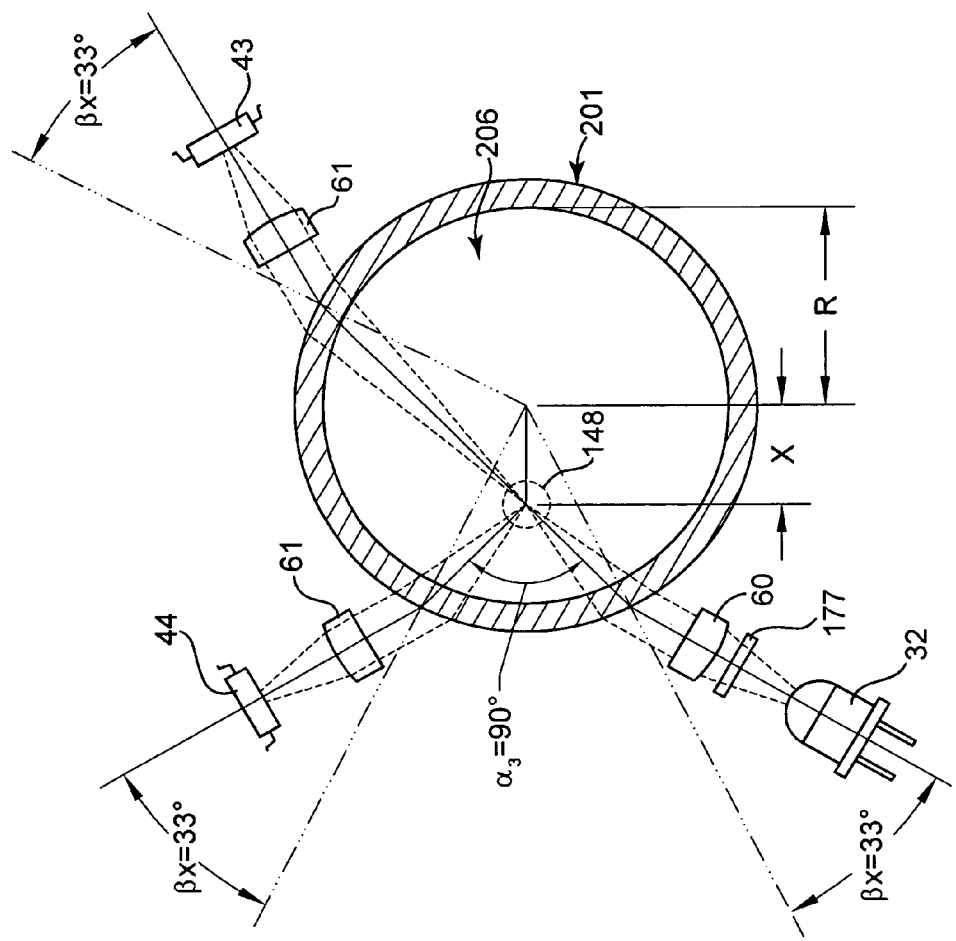
FIG. 11B shows another optical configuration modification with another shifted area of analysis for turbidity measurements.

FIG. 11B shows another optical configuration modification with another shifted area of analysis for turbidity measurements with another shifted area of analysis 178 for turbidity measurements. At least one of an optical axis of excitation focusing optics 60 and an optical axis of sample focusing optics 61 being tilted relatively to a radial direction toward an axis of the vial to shift an area of analysis away from the axis of the cylindrical sample compartment 208. The shifted area of analysis 178 of the turbidity channel is located at least ¼ of radius (R) away from the center of the transparent sample vial 201 or the cylindrical sample compartment 208. $\beta.x = a\sin\{N^*\sin[a\sin(x/R/2)]\} x = 2R\sin[45.\text{degree.}-a\sin(x/R/2)] Gx = 1/(1x) 2$ Where R—radius of vial [0111] N—refractive index of vial glass [0112] x—distance from the vial center to the area of analysis [0113] .beta.x—the incidence angle at the point where excitation beam enters the vial [0114] 1x—distance from the vial wall to the area of analysis [0115] Gx—approximate gain in signal from the shifted area of analysis The incidence angle .beta.x is equal 0.degree. when the area of analysis is in the center axis of the vial 201. An angle of incidence for the excitation beam is set in the range of 10-60 degrees. By adjusting the incidence angle, this embodiment works without the cylindrical negative lenses which adds to the cost and effort to apply. If the vial 201 being made of glass having a refractive index 1.55 and x equals 0.76, the incidence angle .beta.x should be set as 57.degree., i.e., the Brewster angle Fbr, in conjunction with a polarizer 177 which is placed on the optical axis between the light source 32 and the cylindrical vial 201 with the plane of polarization oriented in such a way that the polarization produces zero reflection from the vial wall. Fbr=atan(N). Low reflection from the vial wall gives even better signal to noise ratio. The Brewster angle Fbr is the angle of incidence, on a partially reflecting surface, at which the reflected radiation is fully plane-polarized. It is also the angle of incidence at which the reflected and refracted beams are perpendicular. Polarization by reflection is a refractive property of the surface. .sub.1n.sub.2=tan Fbr The plane of polarization is parallel to the surface. The refracted radiation is partly polarized parallel to the normal. Formerly, the Brewster angle was called the angle of polarization or the polarizing angle.

As the shifted area of analysis 178 is even close to the wall of the vial 201, the light in the modification does not have to travel as far as the original such that the testing range is increased to 4000-5000 NTU and the sensitivity of the second modification can increase 5-10 times as shown in FIG. 12. The IR LED 32 is placed between 8 and 9 o'clock positions, the detector for direct signal measuring 43 is placed at 1 o'clock position, and the detector for scattered signal measuring 44 is placed between 9 and 10 o'clock positions. The turbidity channel of the second modification is also in parallel with the turbidity channel of the first embodiment of the portable multi-channel device of the invention. The detector for scattered signal measuring 44 is placed $\alpha 3=90$ degree to the turbidity channel of the modification, as the detector for scattered signal measuring 44 is placed $\alpha 1=90$ degree to the turbidity channel of the first embodiment of the portable multi-channel device of the invention. By moving the area of analysis closer to the vial wall (smaller R-x) wall, the incidence angle $\beta x$ becomes closer to 90 degrees, reflection for both polarizations becomes higher, and less of the excitation light enters the vial such that the signal to noise ratio eventually goes down (FIG. 12). FIG. 12 shows improvements in the signal to noise ratio for a shifted area of analysis. The larger improvements occurs when $0.5R \leq x \leq 0.8R$, i.e., $0.2R \leq R-x \leq 0.5R$. As shown on graph the gain is different for two different polarizations of the excitation beam. When x is near 0.76R, the incidence angle is approximately equal to the Brewster angle such that the reflection from the vial is minimal.

As mentioned, instead of cylindrical lenses in FIG. 11A, the polarizer 177 is placed between the IR LED 32 and the positive lens 60 in FIG. 11B to provide polarization. The axis of the positive lens 60 tilts counterclockwise from the axis of the turbidity channel of the second modification at an angle .beta.x of 56-58 degrees, while the axis of the positive lens 61 tilts clockwise from the axis of the turbidity channel of the second modification at the angle .beta.x. The axis of the positive lens 61' tilts clockwise from a line perpendicular to the axis of the turbidity channel of the second modification at the angle .beta.x.

The principles, preferred embodiments and modes of operation of the present invention have been described in the foregoing specification. However, the invention, which is intended to be protected, is not limited to the particular embodiments disclosed. The embodiments described herein are illustrative rather than restrictive. Variations and changes may be made by others, and equivalents employed, without departing from the spirit of the present invention. Accordingly, it is expressly intended that all such variations, changes and equivalents that fall within the spirit and scope of the present invention as defined in the claims, be embraced thereby.

What is claimed is:

1. A portable multi-channel device for optically testing of a liquid sample, comprising:
    a sample holder having a sample compartment that holds the liquid sample;
    a turbidity channel that measures turbidity of the liquid sample;
    a second channel that measures one other optical property of the liquid sample, the turbidity channel and the second channel each including:
        a light source placed at a first end of the channel;
        a main detector positioned to receive light emitted by the light source that is transmitted through the sample compartment and the liquid sample;
        a reference detector that measures an intensity of the light emitted by the light source;
        an excitation focusing optic that directs light emitted by the light source into the sample compartment;
        a sample focusing optic that directs transmitted, scattered or fluorescent light from the sample compartment to a second end of the channel;
        an attenuation chamber that attenuates light therein having the reference detector placed at one end, the attenuation chamber connected at 90 degrees at another end thereof to a section of the channel between the light source and the excitation focusing optic;
        a mirror, placed at the second end of the channel, with a reflecting surface tilted 45 degrees from a vertical axis of the sample compartment such that transmitted, scattered or fluorescent light from the sample focusing optic is directed toward the main detector; and;
        a chamber having the main detector placed at one end and connected at 90 degrees at another end thereof to a section of the channel having the reflecting surface of the mirror; and
    a controller that processes signals from the reference detector of the turbidity channel, the main detector of the turbidity channel, and the main detector of the second channel perpendicular to the turbidity channel to evaluate the turbidity of the liquid sample, and that processes signals from the reference detector of the second channel and the main detector of the second channel to evaluate the one other optical property of the liquid sample.

2. The portable multi-channel device of claim 1, wherein the sample compartment has an opening at a bottom thereof for introducing a non-optical sensor unit for testing the liquid sample.

3. The portable multi-channel device of claim 2, wherein the non-optical sensor unit includes at least one of a temperature sensor, a conductivity sensor, and a pH sensor.

4. The portable multi-channel device of claim 1, wherein the sample compartment is water-tight for the sample liquid to pour therein directly.

5. The portable multi-channel device of claim 4, wherein at least the excitation focusing optic directly contacts the sample liquid poured in the sample compartment.

6. The portable multi-channel device of claim 5, wherein the sample focusing optic directly contacts the sample liquid poured in the sample compartment.

7. The portable multi-channel device of claim 4, wherein a non-optical sensor unit is directly placed underneath the sample compartment in a water-tight manner and in contact with the sample solution.

8. The portable multi-channel device of claim 7, wherein the non-optical sensor unit includes at least one of a temperature sensor, a conductivity sensor, and a pH sensor.

9. The portable multi-channel device of claim 7, wherein the non-optical sensor unit is shaped as a disk.

10. The portable multi-channel device of claim 7, wherein signals generated by the non-optical sensor unit are transmitted externally via spring contacts.

11. The portable multi-channel device of claim 1, further including a diaphragm placed in the channel between the light source and the excitation focusing optic.

12. The portable multi-channel device of claim 11, wherein the diaphragm has an opening of 2 mm wide.

13. The portable multi-channel device of claim 1, wherein the light source is an IR LED with an output peak wavelength at 860 nm or an EPA tungsten lamp.

14. The portable multi-channel device of claim 1, wherein the one other optical property measured by the second channel is a color of the in the liquid sample.

15. The portable multi-channel device of claim 1, wherein the one other optical property measured by the second channel is a concentration of chlorine in the liquid sample.

16. The portable multi-channel device of claim 1, wherein the excitation focusing optic includes at least one positive lens.

17. The portable multi-channel device of claim 1, wherein the sample focusing optic includes a positive lens.

18. The portable multi-channel device of claim 1, further comprising a fluoropolymer film placed between the sample focusing optic and the main detector.

19. The portable multi-channel device of claim 1, wherein the light source constantly illuminates the main detector to generate an optical shift of a "zero signal" from 0.5-1 HZ to 15-30 Hz, the zero signal is a signal which corresponds to the optical signal with low intensity as for analyses concentrations of 0 NTU turbidity or the high absorbency as for analyses of 500 Color Units water, or 10 ppm of chlorine, or for 4000 NTU of turbidity.

20. The portable multi-channel device of claim 1, wherein an optical axis of the excitation focusing optic is aligned with an optical axis of the sample focusing optic and perpendicular to a vertical axis of the sample compartment such that an area of analysis of the channel in the sample compartment is located at and around the vertical axis of the sample compartment.

21. The portable multi-channel device of claim 1, wherein the controller is soldered on a controller board where the sample holder is assembled thereon, and the controller board is housed in a housing with a key-pad and a liquid crystal display.

22. The portable multi-channel device of claim 1, wherein the controller is provided on a controller box external to the sample holder and connected to the sample holder via a cable.

23. The portable multi-channel device of claim 1, further comprising a flexible board that wraps around the sample holder, wherein the light source, the main detector, and the reference detector are soldered on the flexible board facing toward the sample holder.

24. The portable multi-channel device of claim 1, further comprising a lamp mounting chamber and a lamp filament, wherein the light source is a tungsten lamp, and the lamp mounting chamber tilts toward the channel.

25. The portable multi-channel device of claim 1, wherein the channels are located on one identical plane inside of the sample holder.

26. The portable multi-channel device of claim 1, wherein the channels are located on different planes inside of the sample holder.

27. A portable multi-channel device for measuring turbidity and color of a water sample, comprising:
   a sample holder having a sample compartment;
   a turbidity channel that measures the turbidity of the water sample using optical scattering in a visible or infrared range of spectra;
   a color channel that measures the color of the water sample using light transmittance in a visible or ultraviolet range of spectra,
   the turbidity channel and the color channel being arranged symmetrically about a vertical axis of the sample compartment and each having a corresponding optical axis perpendicular to and intersecting with the vertical axis of the sample compartment;
   wherein the turbidity channel and the optical channel each include:
      a light source placed at one end of the channel;
      a main detector placed at the other end of the channel;
      an excitation focusing optic that directs light emitted by the light source through the sample compartment towards the main detector; and
      a sample focusing optic that directs transmitted, scattered or fluorescent light from the water sample to the main detector;
   a reference detector set between the turbidity channel light source and the color channel light source that measures intensity of light emitted by the turbidity channel light source and the color channel light source; and
   a controller that processes signals from the reference detectors and the main detectors to evaluate the turbidity and the color in the water sample.

28. The portable multi-channel device according to claim 27, wherein the main detector of the second optical channel for measuring the color also functions as a scattering light detector for measuring turbidity.

29. The portable multi-channel device of claim 1, further including a third channel that measures the chlorine concentration using light transmittance in a visible range of spectra after applying a chemical compound changing color in presence in chlorine.

30. The portable multi-channel device of claim 1, further including a ball lens placed between the main detector and the reflecting surface of the mirror.

31. the portable multi-channel device of claim 14, wherein the light source of the second channel is a green LED with an output peak wavelength at 525 nm.

32. The portable multi-channel device of claim 15, wherein the light source of the second channel is a UV light with an output peak wavelength at 375 nm.

* * * * *